US010744307B2

(12) United States Patent
Subramanian

(10) Patent No.: US 10,744,307 B2
(45) Date of Patent: *Aug. 18, 2020

(54) MULTI-PURPOSE BALLOON CATHETER FOR INTRA CAVITY RADIATION DELIVERY

(71) Applicant: BEST MEDICAL INTERNATIONAL, INC., Springfield, VA (US)

(72) Inventor: Manny R. Subramanian, Frederick, MD (US)

(73) Assignee: BEST MEDICAL INTERNATIONAL, INC., Springfield, VA (US)

( * ) Notice: Subject to any disclaimer, the term of this patent is extended or adjusted under 35 U.S.C. 154(b) by 256 days.

This patent is subject to a terminal disclaimer.

(21) Appl. No.: 15/292,923

(22) Filed: Oct. 13, 2016

(65) Prior Publication Data

US 2017/0028174 A1 Feb. 2, 2017

Related U.S. Application Data

(60) Continuation-in-part of application No. 15/189,396, filed on Jun. 22, 2016, now Pat. No. 10,406,381, (Continued)

(51) Int. Cl.
*A61M 25/10* (2013.01)
*A61N 5/10* (2006.01)
(Continued)

(52) U.S. Cl.
CPC ........ *A61M 25/1011* (2013.01); *A61M 1/008* (2013.01); *A61M 25/0017* (2013.01); (Continued)

(58) Field of Classification Search
CPC .. A61N 5/1014; A61N 5/1015; A61N 5/1016; A61N 5/1002; A61N 2005/1021;
(Continued)

(56) References Cited

U.S. PATENT DOCUMENTS 2,799,273 A * 7/1957 Oddo ................. A61M 25/1011
604/101.05
4,976,266 A 12/1990 Huffman et al.
(Continued)

FOREIGN PATENT DOCUMENTS

JP 2009232882 10/2009
WO WO99/27985 6/1999
(Continued)

OTHER PUBLICATIONS

Astro 2015 Annual Meeting, Ancer Medical, Hialeah, FL, Booth: 489, Print Profile, Oct. 2015, 2 pages.
(Continued)

*Primary Examiner* — Navin Natnithithadha
*Assistant Examiner* — Sunita Reddy
(74) *Attorney, Agent, or Firm* — JanPaul Guzman; John Brosky

(57) ABSTRACT

A multi-purpose balloon catheter includes a catheter having a proximal end portion, a central portion and a distal end portion, a plurality of lumens associated with the catheter extending from the proximal end portion, and a plurality of inflatable balloons positioned in the central portion and/or the distal end portion. Each of the plurality of inflatable balloons is communicatively associated with a corresponding one of the plurality of lumens, the plurality of inflatable balloons being selectively inflated and deflated to position and stabilize the catheter in a cavity for delivery of a treatment. The catheter can include an extraction point associated with a lumen to remove fluids and material from (Continued)

the cavity, and a connector associated with a corresponding lumen adapted to selectively receive one or more of a liquid saline solution, a fluid medium, or a radioactive isotope provided to a corresponding lumen for delivery of the treatment.

13 Claims, 15 Drawing Sheets

Related U.S. Application Data which is a division of application No. 12/889,032, filed on Sep. 23, 2010, now Pat. No. 9,402,980.

(60) Provisional application No. 62/242,972, filed on Oct. 16, 2015.

(51) Int. Cl.
*A61M 1/00* (2006.01)
*A61M 31/00* (2006.01)
*A61M 25/00* (2006.01)

(52) U.S. Cl.
CPC .... *A61M 25/0026* (2013.01); *A61M 25/1002* (2013.01); *A61M 25/10181* (2013.11); *A61M 31/005* (2013.01); *A61N 5/1002* (2013.01); *A61N 5/1014* (2013.01); *A61N 5/1015* (2013.01); *A61N 5/1016* (2013.01); *A61N 5/1071* (2013.01); *A61M 2025/105* (2013.01); *A61M 2025/1045* (2013.01); *A61M 2210/105* (2013.01); *A61M 2210/1064* (2013.01); *A61M 2210/1067* (2013.01); *A61M 2210/1089* (2013.01); *A61M 2210/1475* (2013.01); *A61N 2005/1003* (2013.01); *A61N 2005/1004* (2013.01); *A61N 2005/1018* (2013.01); *A61N 2005/1021* (2013.01); *A61N 2005/1024* (2013.01); *A61N 2005/1025* (2013.01)

(58) Field of Classification Search
CPC .... A61N 2005/1024; A61N 2005/1025; A61N 2005/1003; A61N 2005/1004; A61N 2005/1018; A61N 5/1071; A61M 25/1011; A61M 31/005; A61M 25/0026; A61M 1/008; A61M 25/1002; A61M 2025/1015; A61M 2025/105; A61M 2025/1079; A61M 2210/105; A61M 2210/1064; A61M 2210/1475; A61M 25/0017; A61M 2210/1067; A61M 2210/1089; A61M 25/10181
USPC .......................................... 600/1, 3; 604/328
See application file for complete search history.

(56) References Cited

U.S. PATENT DOCUMENTS

| | | | |
|---|---|---|---|
| 5,623,940 A | 4/1997 | Daikuzono | |
| 5,653,683 A | 8/1997 | D'Andrea | |
| 5,720,717 A | 2/1998 | D'Andrea | |
| 5,782,800 A * | 7/1998 | Yoon | A61B 17/00234 600/207 |
| 5,913,813 A * | 6/1999 | Williams | A61N 5/1015 600/3 |
| 6,119,697 A * | 9/2000 | Engel | A61F 2/0027 128/885 |
| 6,165,199 A * | 12/2000 | Barbut | A61B 17/22 604/22 |
| 6,251,059 B1 | 6/2001 | Apple et al. | |
| 6,447,462 B1 | 9/2002 | Wallace et al. | |
| 6,616,629 B1 * | 9/2003 | Verin | A61M 25/10 600/1 |
| 6,923,754 B2 | 8/2005 | Lubock | |
| 6,955,641 B2 | 10/2005 | Lubock | |
| 6,958,052 B1 * | 10/2005 | Charlton | A61M 25/007 604/102.02 |
| 7,184,827 B1 * | 2/2007 | Edwards | A61M 25/1011 604/21 |
| 7,357,770 B1 | 4/2008 | Cutrer et al. | |
| 7,662,082 B2 | 2/2010 | White et al. | |
| 8,251,884 B2 | 8/2012 | Lubock et al. | |
| 8,277,370 B2 | 10/2012 | Quick | |
| 8,287,442 B2 | 10/2012 | Quick | |
| 8,348,825 B2 | 1/2013 | Partridge et al. | |
| 8,360,950 B2 | 1/2013 | Acosta et al. | |
| 8,568,284 B2 | 10/2013 | White et al. | |
| 8,961,383 B2 | 2/2015 | Parsai et al. | |
| 9,283,402 B2 | 3/2016 | Cutrer | |
| 9,402,980 B2 | 8/2016 | Subramanian | |
| 9,498,644 B2 | 11/2016 | Cutrer | |
| 2003/0032851 A1 | 2/2003 | Apple et al. | |
| 2004/0087827 A1 | 5/2004 | Lubock | |
| 2005/0027157 A1 | 2/2005 | Winkler et al. | |
| 2005/0080313 A1 | 4/2005 | Stewart et al. | |
| 2005/0101824 A1 | 5/2005 | Stubbs | |
| 2005/0182286 A1 * | 8/2005 | Lubock | A61N 5/1015 600/3 |
| 2006/0100475 A1 | 5/2006 | White et al. | |
| 2006/0173233 A1 | 8/2006 | Lovoi | |
| 2006/0212022 A1 | 9/2006 | Gellman | |
| 2007/0106108 A1 | 5/2007 | Hermann et al. | |
| 2007/0167666 A1 | 7/2007 | Lubock et al. | |
| 2008/0215031 A1 * | 9/2008 | Belfort | A61B 17/12099 604/500 |
| 2008/0221384 A1 | 9/2008 | Chi Sing et al. | |
| 2009/0082609 A1 * | 3/2009 | Condado | A61M 25/0075 600/4 |
| 2009/0143634 A1 | 6/2009 | Benson et al. | |
| 2009/0198095 A1 | 8/2009 | Acosta et al. | |
| 2009/0209805 A1 * | 8/2009 | Lubock | A61N 5/1015 600/7 |
| 2009/0254064 A1 | 10/2009 | Boatman | |
| 2009/0264696 A1 | 10/2009 | White et al. | |
| 2009/0312593 A1 | 12/2009 | Drobnik et al. | |
| 2009/0318855 A1 * | 12/2009 | Ehrenreich | A61M 25/1011 604/28 |
| 2010/0069878 A1 | 3/2010 | Parsai et al. | |
| 2010/0191034 A1 | 7/2010 | Cutrer et al. | |
| 2010/0204688 A1 * | 8/2010 | Hoey | A61B 18/04 606/27 |
| 2010/0331601 A1 | 12/2010 | Partridge et al. | |
| 2011/0034976 A1 | 2/2011 | Mon et al. | |
| 2011/0152683 A1 * | 6/2011 | Gerrans | A61B 17/22012 600/435 |
| 2012/0253099 A1 | 10/2012 | Mon et al. | |
| 2013/0030411 A1 * | 1/2013 | Kreck | A61F 7/12 604/514 |
| 2014/0066896 A1 * | 3/2014 | Tilson | A61F 2/958 604/509 |
| 2014/0257092 A1 | 9/2014 | Lamoureux et al. | |
| 2014/0275712 A1 * | 9/2014 | D'Andrea | A61N 5/1028 600/2 |
| 2014/0277466 A1 * | 9/2014 | Teisen | A61F 2/441 623/17.12 |
| 2019/0117519 A1 * | 4/2019 | Schmid-Schonbein | A61B 5/037 |

FOREIGN PATENT DOCUMENTS

| | | |
|---|---|---|
| WO | WO2008124149 | 10/2008 |
| WO | WO2013049827 | 4/2013 |

OTHER PUBLICATIONS

Gilad N. Cohen et al., "Design of a Novel Applicator for Esophageal High Dose Rate Brachytherapy", Abstract PO51, Abstracts / Brachytherapy, vol. 14, 2015, pp. S101-S102.

(56) References Cited

OTHER PUBLICATIONS

"What is Esophageal Brachytherapy" Ancer Medical, Available at: http://www.ancermedical.com/wp-content/uploads/2016/04/Esophageal-Applicator.pdf, 2016, 6 pages.
Esophageal Applicator (E-AppTM), Ancer Medical, 2016, 1 page.
Anorectal Applicator (AR) TM, Ancer Medical, 2016, 2 pages.
Esophageal Applicator (E-App)TM, Ancer Medical, Available at: http://www.ancermedical.com/wp-content/uploads/2016/04/Esophageal-Applicator.pdf, 2016, 5 pages.
"Hologic takes SenoRx assets in out-of-court settlement with C.R. Bard", A. Sarvestani, www.massdevice.com, Aug. 14, 2013 (downloaded,Oct. 19, 2015), 4 pages.
"Best Dual Balloon Breast Brachytherapy Applicator", from TeamBest brochure/material, Sep. 13, 2014, 3 pages.
U.S. Appl. No. 15/189,396, filed Jun. 22, 2016, Subramanian.
U.S. Appl. No. 15/293,342, filed Oct. 14, 2016, Subramanian.
U.S. Appl. No. 12/889,032, filed Sep. 23, 2010, Subramanian.

* cited by examiner

MULTI-PURPOSE BALLOON CATHETER FOR INTRA CAVITY RADIATION DELIVERY

CROSS-REFERENCE TO RELATED APPLICATIONS

This application claims priority under 35 U.S.C. § 120 to and is a continuation-in-part (CIP) of U.S. patent application Ser. No. 15/189,396, filed on Jun. 22, 2016, which is a divisional application of U.S. patent application Ser. No. 12/889,032, filed on Sep. 23, 2010, and this application also claims priority under 35 U.S.C. § 119 to U.S. Provisional Patent Application No. 62/242,972, filed on Oct. 16, 2015, all of which are hereby incorporated herein by reference in their entirety.

FIELD OF THE INVENTION

The invention generally relates to the field of medical devices, and more particularly to a multi-purpose balloon catheter having a plurality of balloons for selectively stabilizing and positioning the catheter, and for delivering a radiation dose, and can also assist in measuring and imaging internal organs, cavities and removing bodily fluids or material while providing an easy connection module for treatment.

BACKGROUND

A catheter is a tube that can be inserted into a body cavity, duct, or vessel. Catheters thereby allow drainage, injection of fluids, or access by surgical instruments. The process of inserting a catheter is catheterization. In most uses, a catheter is a thin, flexible tube ("soft" catheter), though in some uses, it is a larger, solid ("hard") catheter. A catheter left inside the body, either temporarily or permanently, may be referred to as an indwelling catheter. A permanently inserted catheter may be referred to as a Permcath®, for example.

The ancient Syrians created catheters from reeds. "Katheter—καθετηρ" originally referred to an instrument that was inserted such as a plug. The word "katheter" in turn came from "kathiemai—ηαθιεμαι" meaning "to sit". The ancient Greeks inserted a hollow metal tube through the urethra into the bladder to empty it and the tube came to be known as a "katheter".

Heretofore various balloon type catheters and perfusion catheters have been proposed for performing one or two procedures. However, heretofore, prior to the present invention a multi-purpose balloon catheter capable of performing two or more procedures has not been available.

The incidence of esophageal and stomach cancers continue to increase globally. Often patients die without proper diagnosis and/or treatment. For localized cancers, tumors can be first shrunk with the help of high dose rate brachytherapy employing appropriate applicators. This can be followed by surgical, chemotherapeutic and/or biological agents or mediated targeted therapeutic procedures. Positioning and targeting of radiation to the site of disease with minimal or no damage to normal nearby organs remains a challenge. Thus, the need exists to have a catheter that can not only provide multiple functions but also can be selectively positioned and targeted for delivering the radiation or other suitable treatment modalities and other applications such as rectal, bladder, colon, uteral, cervical and breast cancers. The catheters of the present invention can address that need as well as can promote minimizing risk of causing damage to surrounding tissue or can promote reducing pain during a treatment procedure.

Thus, a multi-purpose balloon catheter for intra cavity radiation delivery addressing the aforementioned problems is desired.

SUMMARY OF INVENTION

A multi-purpose balloon catheter includes a single intra-cavity catheter having a proximal end portion, a central portion and a non-branching distal end portion, a plurality of lumens positioned in association with the catheter extending from the proximal end portion, and a plurality of inflatable balloons arranged in a plurality of independent and, distinct balloons groups. Each of the plurality of inflatable balloons are positioned in association with one or more of the central portion and/or the non-branching distal end portion of the single intra-cavity catheter. Each of the plurality of inflatable balloons is communicatively connected to a corresponding one of the plurality of lumens, the plurality of inflatable balloons being selectively inflated or deflated to position and/or stabilize the catheter in a cavity for delivery of a treatment or the plurality of inflatable balloons being configured to be selectively filled with a treatment medium, such as a radioactive material, or Contrast medium, for a treatment.

The muni-purpose balloon catheter can include a secondary treatment balloon positioned at the non-branching distal end portion of the single intra-cavity catheter and communicatively connected to one or more of the plurality of lumens, and at least one of the plurality of lumens is adapted to provide a medium to selectively inflate and deflate the secondary treatment balloon to selectively position and/or stabilize the secondary treatment balloon for delivery of the treatment and another of the plurality of lumens adapted to deliver a radioactive dose or a therapeutic agent or therapeutic medium for the treatment. In addition, a radioactive wire can be inserted into one of the lumens to deliver radiation to an internal organ or cavity of a patient. The multi-purpose catheter can further include a marker placed in assnciation with the non-branching distal end portion of the single intra-cavity indicate position of the catheter.

These and other features of the present invention will become readily apparent upon further review of the following specification and drawings.

DESCRIPTION OF THE DRAWINGS

Unless otherwise indicated, similar reference characters denote corresponding features consistently throughout the attached drawings.

DETAILED DESCRIPTION

The present disclosure relates to a multi-purpose balloon catheter for delivering radiation and for targeting single to multiple disease sites with a novel multi balloon configuration Additionally, the multti-purpose balloon catheter enables fixing or positioning radioactive wires or radioactive material in a cavity, such as in the espphagus, in other organs or in a surgically created cavity, to deliver radiation or a therapeutic agent to a targeted portion using a conformable device including balloons, lumens and a single intra-cavity catheter. Moreover, the multi-purpose balloon catheter allows for dianosing the anatomy of an adnormal organ shape by evaluating the balloon shape (with contrast agent) by comparing to shapes of normal healthy patient organs. The multi-purpose balloon catheter allows treatment of multiple sites with diseases using the same device (esophageal and stomach cancers). Finally, the multi-purpose balloon catheter allows for the treatment of one organ while determining the does delivered to a nearby normal organ with a small dosimeter (MOSFET system).

Figure 1A:
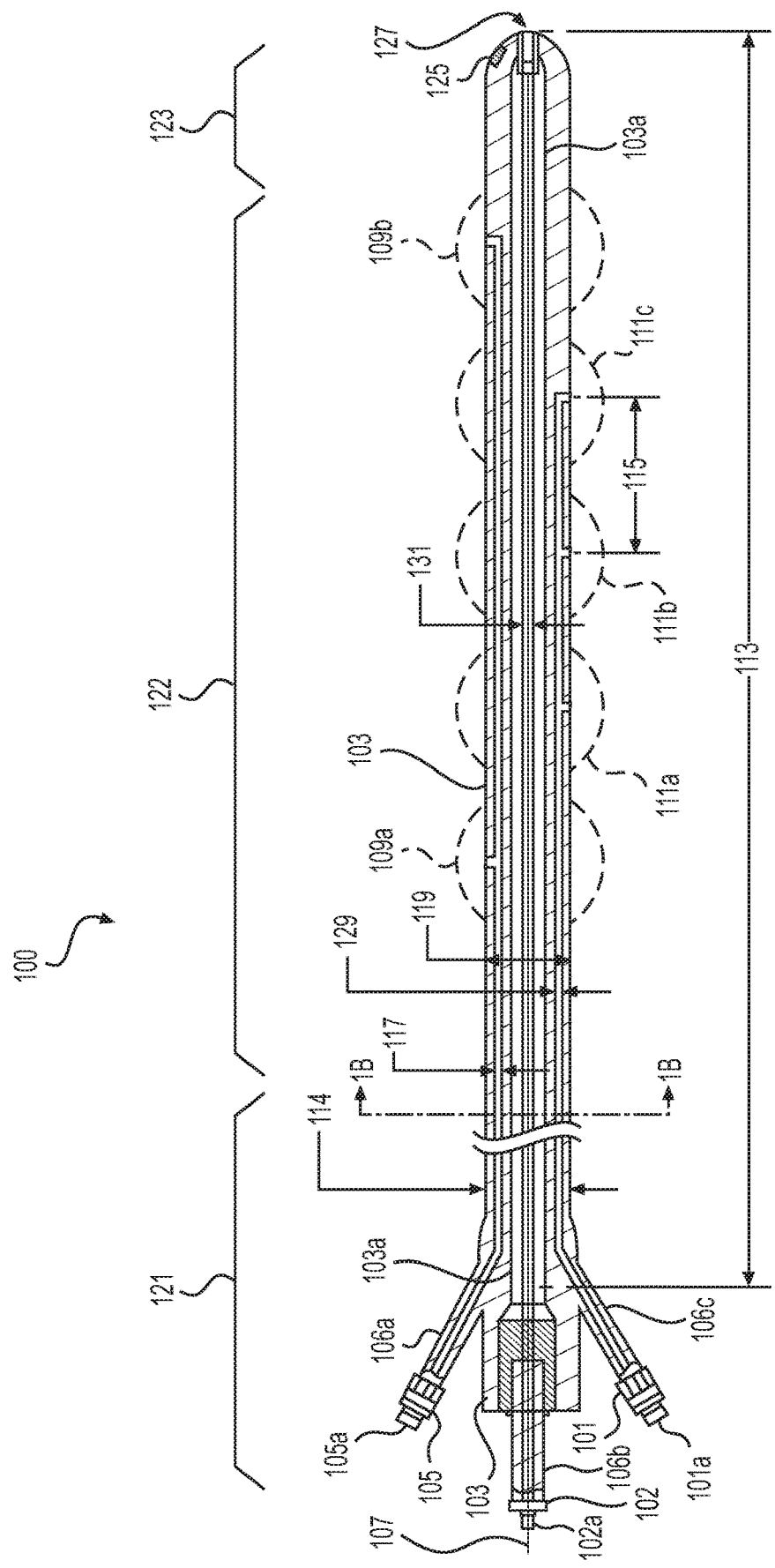
FIG. 1A is a longitudinal plan view of an embodiment of a multi-purpose balloon catheter according to the present invention.

Referring now to the drawings in greater detail, there is illustrated in FIG. 1A, an embodiment of a multi-purpose balloon catheter 100 according to the teachings of the invention. The multi-purpose balloon catheter 100 includes a proximal end portion 121, a central portion 122 as can include a generally tubular shaped body 103, and a non-branching distal end portion 123, with the non-branching distal end portion 123 including an a suitable marker such as an X-ray marker 125 to indicate a position of the non-branching distal end portion 123 of the multi-purpose balloon catheter 100. The X-ray marker 125 typically can be gold, lead, tungsten or other heavy metal suitable for X-ray visualization, or can be other suitable material, as can depend on the use or application, and should not be construed in a limiting sense.

The multi-purpose balloon catheter 100 can be made of various suitable materials, such as a polymeric material, such as a polyurethane or a polyacrylic material, among other examples, as can depend on the use or application, for example. Typically, a length 113 of the multi-purpose balloon catheter 100 of FIG. 1A is about 78 cm to the tip from the base area of the multi-purpose balloon catheter 100, but the catheter 100 can be of various suitable lengths and dimensions, as can depend on the use or application, for example. A diameter 114 of the catheter 100 of FIG. 1A is typically 0.45 cm, but can be of various suitable diameters, as can depend on the use or application, for example.

The proximal end portion 121 of the catheter 100 includes the plurality of neck portions 106a, 106b, and 106c, made of similar suitable material as the catheter 100. The neck portions 106a, 106b, and 106c each include a corresponding lumen 101a, 102a and 105a therein that extends within the catheter 100 for balloon inflation or for treatment delivery, for example. The neck portions 106a, 106b, and 106c and corresponding lumens 101a, 102a and 105a are desirably associated with a corresponding suitable connector or connecting mechanism 101, 102 and 105, such as suitable luer locks 101, 102, and 105, that can be a male or a female connection, for example.

For example, the luer-locks 101 and 105 can be fitted with syringes for selectively inflating balloons 111a, 111b, and 111c and balloons 109a and 109b to a predetermined size, for a particular use or application, for example. The balloons 111a, 111b, and 111c and the balloons 109a and 109b being desirably located in the central portion 122 to facilitate positioning and stabilizing the catheter 100 for delivery of a treatment. In the catheter 100, the lumen 101a associated with the luer lock 101 can receive and remove a fluid medium, such as saline solution or a gaseous medium, such as by a syringe or other suitable delivery mechanism, such as a pump, to selectively inflate and deflate the balloons 111a, 111b, and 111c.

Similarly, the lumen 105a associated with the luer lock 105 can receive and remove a fluid medium, such as saline solution or a gaseous medium, such as by a syringe or other suitable delivery mechanism, such as a pump, to selectively inflate and deflate the balloons 109a and 109b, for example. The locking mechanism or connector, such as provided by the luer locks 101, 102 and 105, when affixed to the catheter 100 can provide for selectively not allowing or selectively allowing a fluid medium, such as including fluids, fluid or gaseous mediums, or air, or allowing a contrast medium, for example, to pass through a corresponding connecting point provided by the connector or connecting mechanism 101, 102 and 105, such as luer locks, with the catheter 100.

As depicted in FIG. 1A, the central lumen 102a associated with the connector 102, such as a luer lock, can be used to insert a radioactive wire 107 as a radiation source or a radioactive material into the treatment catheter 100, such radiation source or radioactive material can also include a radioactive seed, for treatment at a specific site or at a predetermined location of the organ or cavity. Also, the central lumen 102a associated with the locking mechanism or connector 102, such as a luer lock, can be used with suction or a syringe to remove bodily fluids or material from a cavity in a body, such as an area adjacent to the cavity, using the treatment catheter 100, such as by communicating with an extraction opening 127 at the distal end portion 123 of the catheter 100, such as illustrated in FIG. 1A, for example. The central lumen 102a can be positioned in a larger main lumen 103a extending through the catheter 100, as illustrated in FIG. 1A. The locking mechanism or connector 102 for the lumen 102a can allow for a relatively easier controlled delivery and guidance for treatment and extraction within a treatment area, for example.

Selectively inflating the balloons 109a, 109b, 111a, 111b and 111c can allow for selectively positioning and/or stabilizing the catheter 100 or for administration of a therapeutic treatment or for removal of bodily fluids or material in a cavity, such as in a bodily organ or in a cavity region, such as the esophagus, rectum, stomach or a surgically created cavity, such as in the breast or other organ or bodily tissue, such as through the lumen 102a, for example. The lumens 101a and 105a and the inflated balloons 109a, 109b, 111a, 111b and 111c can contain a contrast liquid or other contrast medium, such as for contrast purposes in imaging applications, as cart also be used for inflation of the balloons 109a, 109b, 111a, 111b and 111c, for positioning, stabilization and treatment, for example. As illustrated in FIG. 1A, the balloons 109a, 109b, 111a, 111b and 111c can be arranged in a plurality of independent and distinct balloon groups in association with the central portion 122 of the catheter 100. For example, illustrated in FIG. 1A, the balloons 109a and 109b can form a first balloon group, and the balloons 111a, 111b and 111c can form a second balloon group. Each independent and distinct balloon group can be selectively inflated or deflated or can also receive and can have removed a contrast liquid or other contrast medium independently of the balloons of another balloon group, such as through corresponding ones of the plurality of connectors, such as connectors 101 and 105, and through the associated corresponding ones of the plurality, of the lumens, such as lumens 101a and 105a, for example.

As discussed herein, the catheter 100 includes a plurality of balloons, such as the balloons 109a, 109b, 111a, 111b and 111c that may be arranged in a plurality of independent and distinct balloons groups, such as the first balloon group including balloons 109a and 109b and the second balloon group including balloons 111a, 111b and 111c. The lumens of the catheter 100, such as the lumens 101a and 105a, can be communicatively connected to a single or to any of various pluralities of balloons. For example, the lumen 101a can be connected with balloons 111a, 111b, 111c of the second balloon group and the lumen 105a can be connected to balloons 109a and 109b of the first balloon group, as illustrated in FIG. 1A, for example. Also, the catheter 100 can have any of various other suitable connection arrangements with more or less lumens or balloons, as can depend on the use or application, for example. Further, the balloons, such as the balloons 109a, 109b. 111a, 111b and 111c, can have any of various suitable sizes or shapes, such as cylindrical, spherical, oval, oblong, toroidal, or other suitable shapes, as can depend on the use or application, for example.

The lumens, such as the lumens 101a, 102a and 105a, can have any of various suitable sizes, shapes or configurations, such as cylindrical, rectangular, oval, or other suitable shapes or configurations, as can depend on the use or application, for example. Also, a typical dimension of a diameter of the lumens, such as indicated at 117 for diameter of the lumen 105a, as indicated at 129 for a diameter of the lumen 101a, and as indicated at 131 for a diameter of the lumen 102a, for inflating the balloons 109a, 109b, 111a, 111b and 111c and/or for delivery of a treatment, can be typically in a range of from about 0.8 mm to about 1.5 mm, for example, but can be of various suitable dimensions, as can depend on the use or application, and should not be construed in a limiting sense.

Further, the spacing between each of the centers of adjacent ones of the balloons 109a, 109b, 111a, 111b and 111c, as can desirably correspond to the spacing between adjacent exit points of the lumens 101a and 105a respective adjacent balloons, can be a same or a different spacing, as can depend on the use or application, such as desirably being spaced apart by about 2.5 cm from each other as indicated at 115, for example. The first balloon group including the balloons 109a and 109b is independently arranged from the second balloon croup including the balloons 111a, 111b and 111c on the catheter 100 along the length 113 catheter 100, such as illustrated in FIG. 1A. Also, the lumens, such as the lumens 101a, 102a and 105a, can be positioned within an interior of the catheter 100, such interior of the catheter 100 being indicated by the numeral 119, or can be positioned or integrally formed on or in a exterior surface or layer of the catheter 100, for example, as can depend on the use or application, for example.

The balloons, such as the balloons 109a, 109b, 111a, 111b and 111c, can be made of nylon, polyurethane, Polyether block amide Pebax®, poly(ethylene terephthalate), commonly abbreviated PET or other thermoplastic elastomers or other suitable materials, as can depend on the use or application, for example. Additionally, one or more of the balloons 109a, 109b, 111a, 111b and 111c and all or part of the catheter 100, such as the body 103 of the central portion 122 of the catheter 100, can be coated or impregnated with various suitable coatings for ease of assembly such as a silicone type coating, or the balloons can be impregnated or coated with various suitable therapeutic or medicinal agents for treatment at a site within the body, such as by elution of the agent from the balloon or the catheter, for example.

In an embodiment, the catheter 100, as well as the balloons associated with the catheter 100, such as the balloons 109a, 109b, 111a, 111b, and 111c, can be uncoated or can be coated with a lubricant for lubrication for ease of positioning the catheter 100 at a treatment site, or can be coated or formed with antimicrobial or medicinal agents for delivery of a therapeutic treatment at the treatment site, for example. In this regard, in various embodiments of catheters, such as the catheter 100, various therapeutic drugs can be coated onto the surface of the balloons or catheter for releasing the drug internally to a specific location of the cavity being treated.

The catheter 100 of FIG. 1A having a plurality of connectors or locking mechanisms, such as the luer-locks 101, 102 and 105 as examples of connectors or locking mechanisms, and a plurality of balloons, such as the balloons 109a, 109b, 111a, 111b, and 111c, can be inserted into various body cavities, such as the esophagus, but is not limited thereto and can also be inserted for treatment into other cavities, such as the rectum, vagina, etc. or surgically created cavities, wherein the radioactive wire, radioactive seed or other radioactive or therapeutic material or other therapeutic agent, can provide the requisite radiation dose or therapeutic treatment to treat cancerous growth or other medical conditions. Typically, the dimension of the radioactive wire, such as the radioactive wire 107, that can be inserted into the lumen 102a, is desirably in a range of about 0.5 mm to about 0.8 mm, for example, but can be of various suitable dimensions and configurations, as can depend on the use or application.

Desirably, the radioactive wire, such as the radioactive wire 107, is made of a suitable radioactive material, such as can include Iridium-192, Cobalt 60 and Yttrium 168, for example. The high dose rate (HDR) treatment delivered through the catheter, such as the catheter 100, can be conducted with Ir-192, Au-198, 1-125 and Cs-131, for example. Typically the dose of radiation delivered by the radioactive wire, such as the radioactive wire 107, is about 1 Curie to about 10 Curies per seed, but can be any suitable dose, as can depend on the use or application. Also, HDR afterloaders can be used in conjunction with embodiments of the catheters, such as the catheter 100, for delivery of a radiation dose for treatment, such as Varisource, Gamma Med and BEBIG afterloaders or other suitable afterloaders, for example.

For a low dose rate (LDR) application delivered through embodiments of catheters, such as the catheter 100, Sr-90 can be used in conjunction with the radiation wire, such as the radioactive wire 107, as well as Cs-131 and Yb-168 can be used as the radiation source, for example. Typically the dose of radiation using the LDR configuration is usually one thousand times less than the HDR applications, such LDR dose being in a range of about 1 milli Curie to about 10 milli Curies, for example.

An advantage, among others, of embodiments of catheters, such as the catheter 100, is that it can allow for delivering the radiation dose to a specific or a predetermined site or location of or in the cavity, such as in an organ, a body cavity or a surgically created cavity, such as by the radioactive wire 107, through the lumen 102a, and can also allow, at the same time or at different times, for the removal of fluid or bodily material, from the area of the treatment site, such as through the lumen 102 or the main lumen 103a, for example, while also providing enhanced stabilization and positioning of the catheter, such as the catheter 100, for treatment, by selective inflation and deflation of the corresponding balloons, such as the balloons 109a, 109b, 111a, 111b, and 111c, for example, as can allow to selectively controlling the size of each balloon independently or in conjunction with one or more other balloons, to selectively adjust the location and for positioning of the catheter at the treatment site.

Figure 1B:
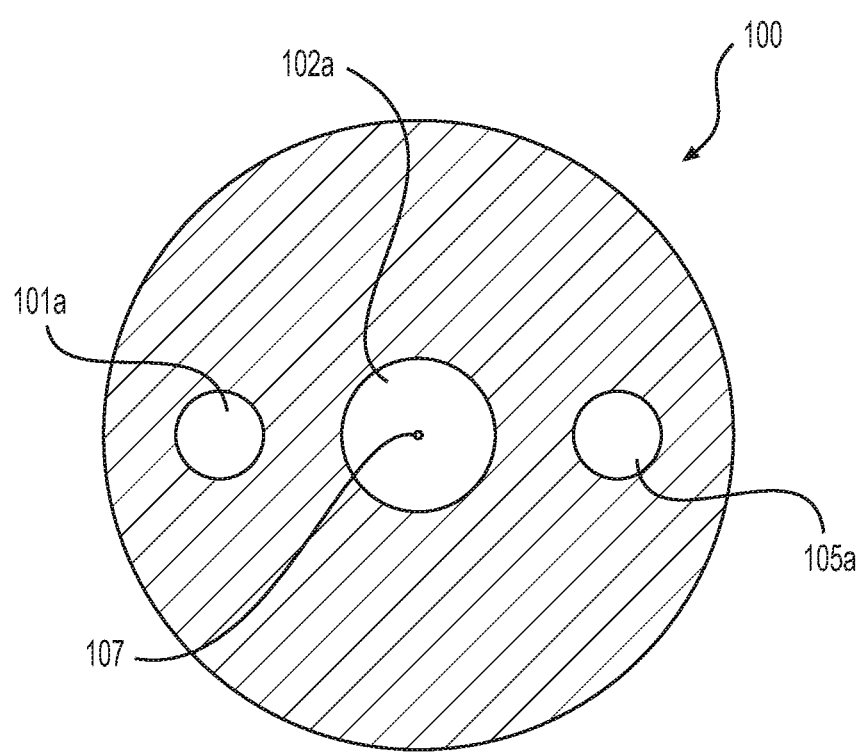
FIG. 1B is a cross-sectional view taken along lines 1B-1B of FIG. 1A.

FIG. 1B shows the cross sectional view taken along the 1B-1B plane of the catheter 100 of FIG. 1A. The catheter 100 is illustrated in section in FIG. 1B along with relative positions of the lumens 101a, 102a and 105a, for example. Also, FIG. 1B illustrates a relative position of the radioactive wire 107 within the lumen 102a. The central lumen 102a allows for selectively inserting and positioning the radioactive wire, such as the radioactive wire 107, a radioactive seed or other suitable treatment medium, for delivery of a treatment, for example.

Figure 1C:
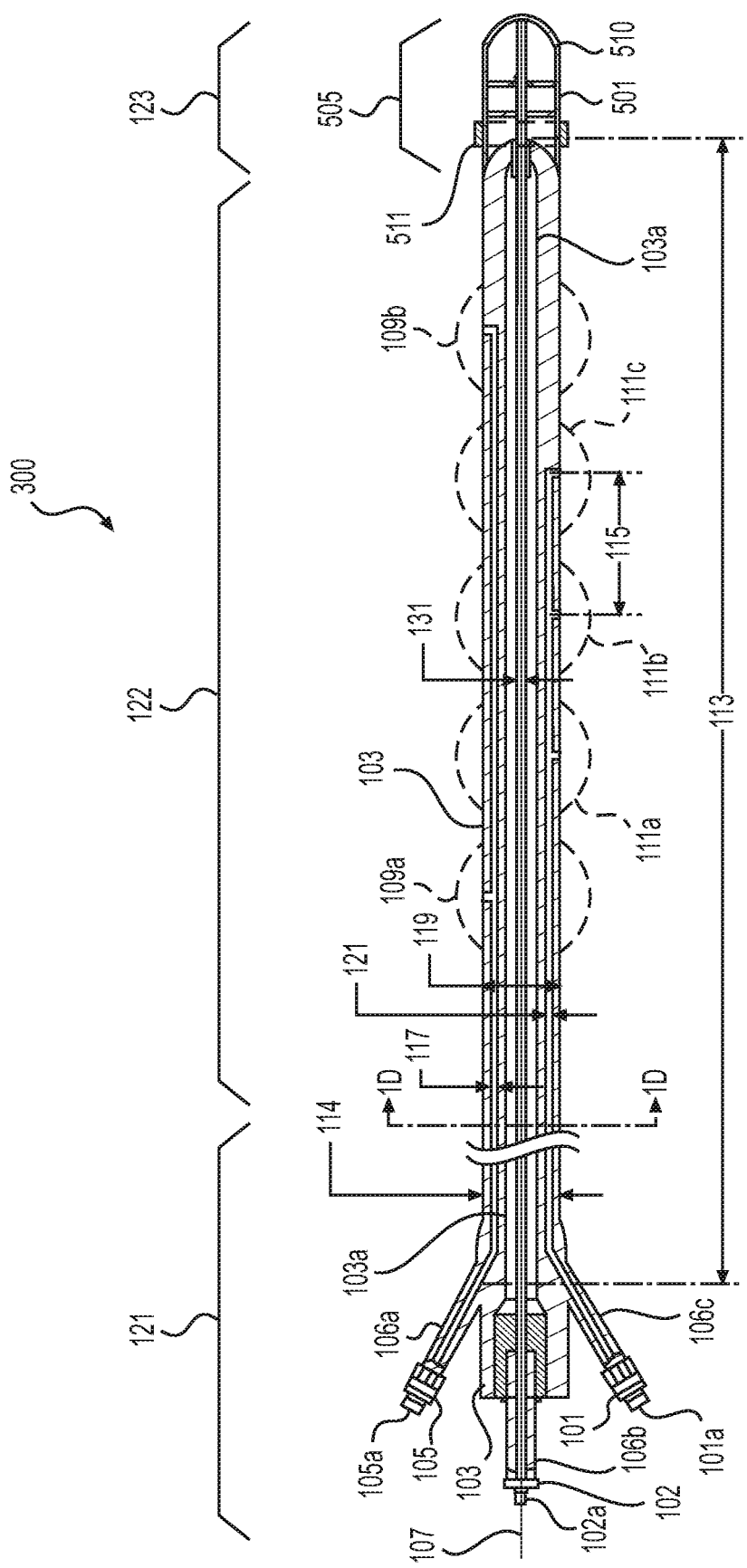
FIG. 1C is a plan view of an embodiment of a multi-purpose balloon catheter according to the present invention having an embodiment of an applicator extender in association with the distal position of the catheter.

Referring to FIG. 1C, another embodiment of a multi-purpose balloon single intra-cavity catheter 300 is illustrated. The catheter 300 is similar to the catheter 100 of FIG. 1A, as described, including the balloons 109a, 109b, 111a, 111b, 111c, and the corresponding lumens 101a, 102a and 105a with the connectors or locking mechanisms 101, 102 and 105, as described, and can be of suitable shapes, dimensions and materials, as described in relation to the catheter 100. However, the catheter 300 also includes an embodiment of an applicator extender 505 at the distal end portion 123 of the catheter 300. The applicator extender 505 includes a lower portion or a lower chamber 501 and an upper portion or an upper chamber 510 for delivering a radiation dose, such as to the esophagus, such as through the radioactive wire 107, for example.

A secondary treatment radiation balloon wire can be inserted into the applicator extender 505 through the middle section having a membrane that can be made of silicone, as can also deliver a treatment fluid or treatment medium, for example. The applicator extender 505 can be associated with or include a suitable connector or fastening mechanism 511, such as a suitable luer lock, to allow fitting the applicator extender 505 with the catheter 300 in association with the distal end portion 123 of the catheter 300 end, such as in FIG. 1C, for example. The applicator extender 505 in conjunction with an embodiment of a treatment balloon is illustrated in greater detail and further described herein in relation to FIGS. 1F, 1G and 1H.

Figure 1D:
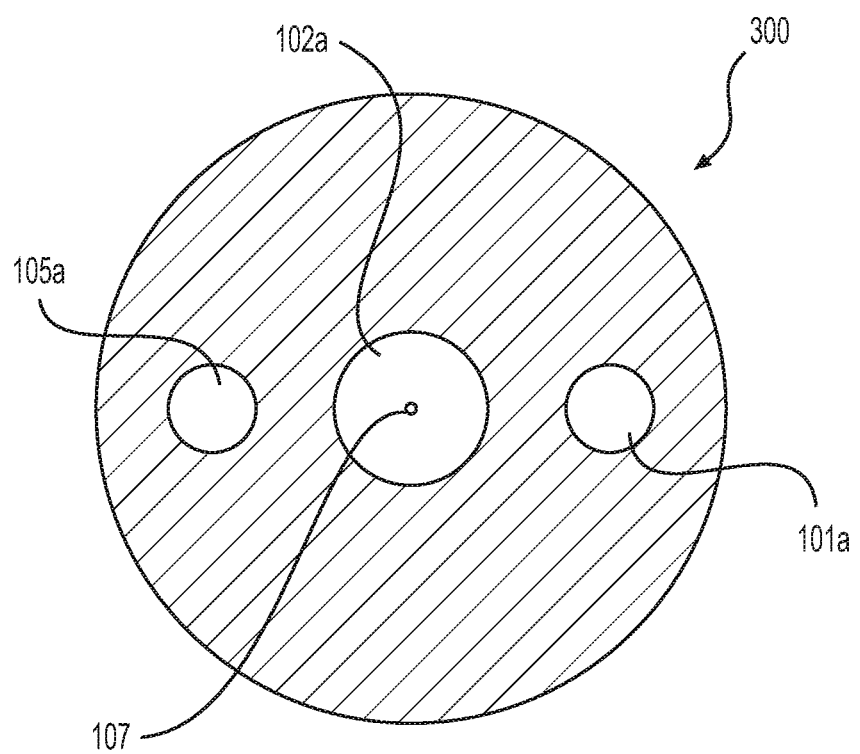
FIG. 1D is a cross-sectional view taken along lines 1D-1D of the embodiment of the catheter of FIG. 1C.

FIG. 1D illustrates is a cross sectional planar view taken along the 1D-1D plane of the catheter 300 of FIG. 1C. The catheter 300 is illustrated in section in FIG. 1D along with relative positions of the lumens 101a, 102a and 105a, for example. Also, FIG. 1D illustrates a relative position of the radioactive wire 107 within the lumen 102a. The central lumen 102a allows for selectively inserting and positioning the radioactive wire, such as the radioactive wire 107, or other suitable treatment medium, for delivery of a treatment, for example.

Figure 1E:
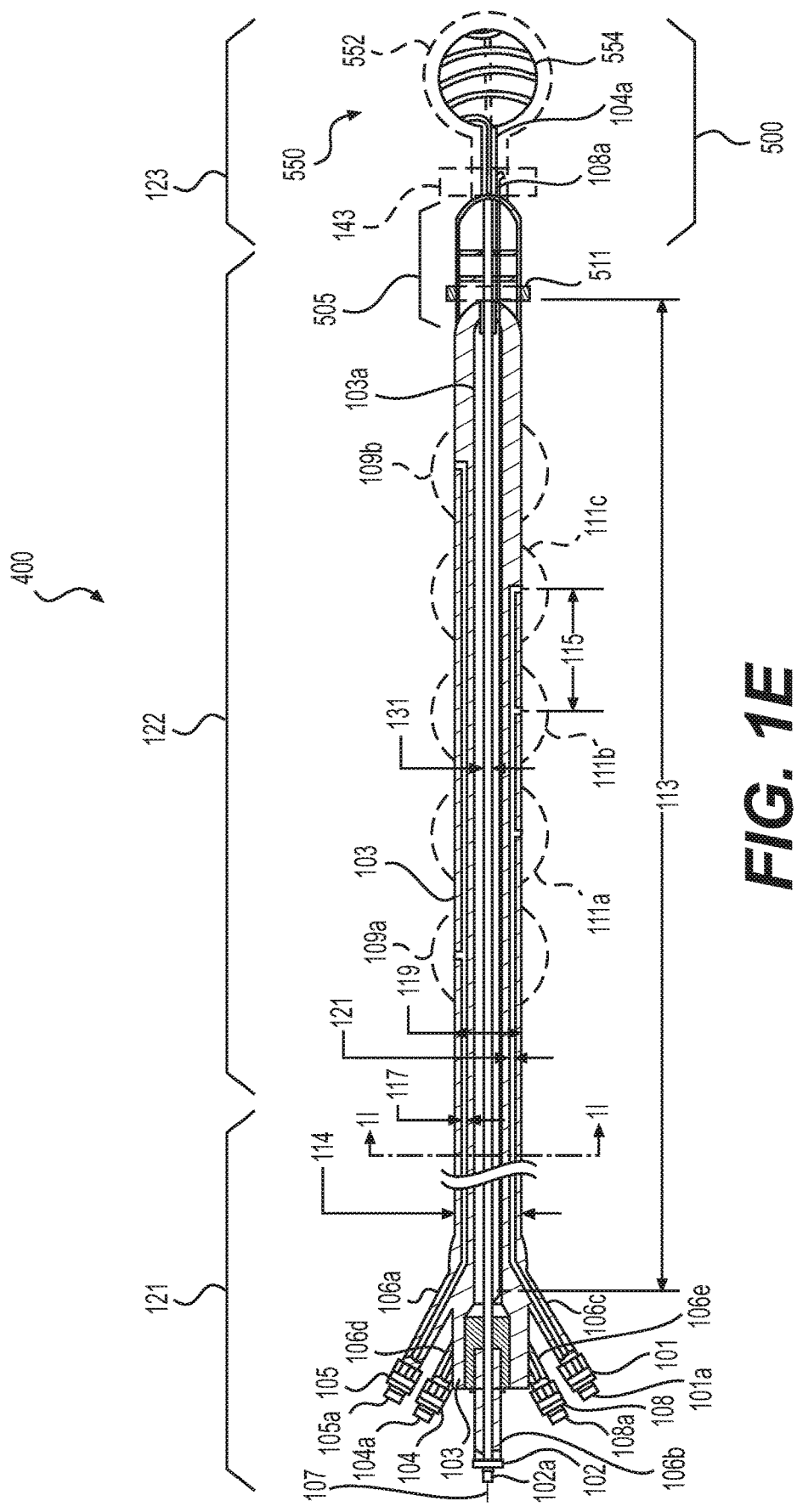
FIG. 1E is a plan view of an embodiment of a multi-purpose balloon catheter according to the present invention having a treatment balloon configuration and an embodiment of an applicator extender in conjunction with an embodiment of a treatment balloon.

Referring to FIG. 1E, another embodiment of a multi-purpose balloon single intra-cavity catheter 400 is illustrated. The catheter 400 is similar to the catheter 100 of FIG. 1A and the catheter 300 of FIG. 1C, as described, including the balloons 109a, 109b, 111a, 111b, 111c, and the corresponding lumens 101a, 102a and 105a with the connectors or locking mechanisms 101, 102, and 105, as described, and can be of suitable shapes, dimensions and materials, as described in relation to the catheters 100 and 300. However, the catheter 400 also includes an embodiment of an applicator extender balloon assembly 500 at the distal end portion 123 of the catheter 400 that includes the applicator extender 505, such as also illustrated in FIG. 1C, and an embodiment of a secondary treatment balloon 550.

The applicator extender 505 provides a connection with the lumen 102a for delivery of a radiation dose, or for delivery of a therapeutic agent, to the secondary treatment balloon 550 for a treatment, such as to a cavity formed by or in the stomach or a surgically created cavity, such as through the radioactive wire 107, for example. A secondary treatment radiation balloon wire, such as the radioactive wire 107, can be inserted into the lumen 102a and through the applicator extender 505 through the middle section having a membrane that can be made of silicone, and can also deliver a treatment fluid or treatment medium, for example, to the secondary treatment balloon 550.

The secondary treatment balloon 550 includes an outer secondary treatment balloon 552 and an inner secondary treatment balloon 554. The outer secondary treatment balloon 552 and the inner secondary treatment balloon 554 can be selectively inflated and deflated to be positioned in a body cavity or a surgically created cavity to be treated and the inner balloon 554 is associated with at least one secondary treatment lumen communicatively connected with the lumen 102a for delivery and removal of a radiation dose, a therapeutic agent or other treatment, to be further described in relation to FIGS. 1F, 1G and 1H.

Additionally, the catheter 400 includes neck portions 106*d* and 106*e* and corresponding lumens 104*a* and 108*a* are desirably associated with a corresponding suitable connector or connecting mechanism 104 and 108, such as suitable luer locks 104 and 108, which can be a male or a female connection, for example. The lumens 104*a* and 108*a* can be extended through the applicator extender 505, such as by a suitable connector lumen in the applicator extender 505, to be placed in communication with the secondary treatment balloon 550. The lumen 104*a* is communicatively positioned in association with/connects with the inner secondary treatment balloon 554 and the lumen 108*a* is communicatively positioned in association with/connects with the outer secondary treatment balloon 552 to respectively selectively inflate or deflate the inner secondary treatment balloon 554 and the outer secondary treatment balloon 552 to position and stabilize the secondary treatment balloon 550 in a body cavity to be treated.

Similarly, the lumens 104*a* and 108*a* associated with the luer locks 104 and 108, respectively, can receive and remove a fluid medium, such as saline solution or a gaseous medium, such as by a syringe or other suitable delivery mechanism or machine, such as a pump, to selectively inflate or deflate the inner secondary treatment balloon 554 and the outer secondary treatment balloon 552, to provide a corresponding balloon; shape, size and configuration in the body cavity for the treatment, for example.

Additionally, the applicator extender 505 can be associated with or include a suitable connector or fastening mechanism 511, such as a suitable luer lock, to allow fitting with the catheter 400 in association with the distal end portion 123 of the catheter 400, such as in FIG. 1E, for example. The applicator extender 505 and the secondary treatment balloon 550 can be associated with a further connector or locking mechanism 143, such as a luer lock, to allow selective fitting the applicator extender 505 with the secondary treatment balloon 550 to allow for secondary treatment balloons 550 of different sizes, shapes and configurations to be communicatively connected with the applicator extender 505 for delivery of a treatment, for example.

Also, the applicator extender 505 and the secondary treatment balloon 550, as well as the applicator extender balloon assembly 500, can be integrally formed together with each other and with the catheter 400, or can also suitably be joined together by other suitable processes and methods, such as with a suitable adhesive, glue or tape in addition to the locking mechanism or connector, such as the luer locks 511 and 143, for example. The applicator extender balloon assembly 500 including the applicator extender 505 and various exemplary embodiments of the secondary treatment balloon 550 are illustrated in greater detail and further described herein in relation to FIGS. 1F, 1G and 1H.

Figure 1F:
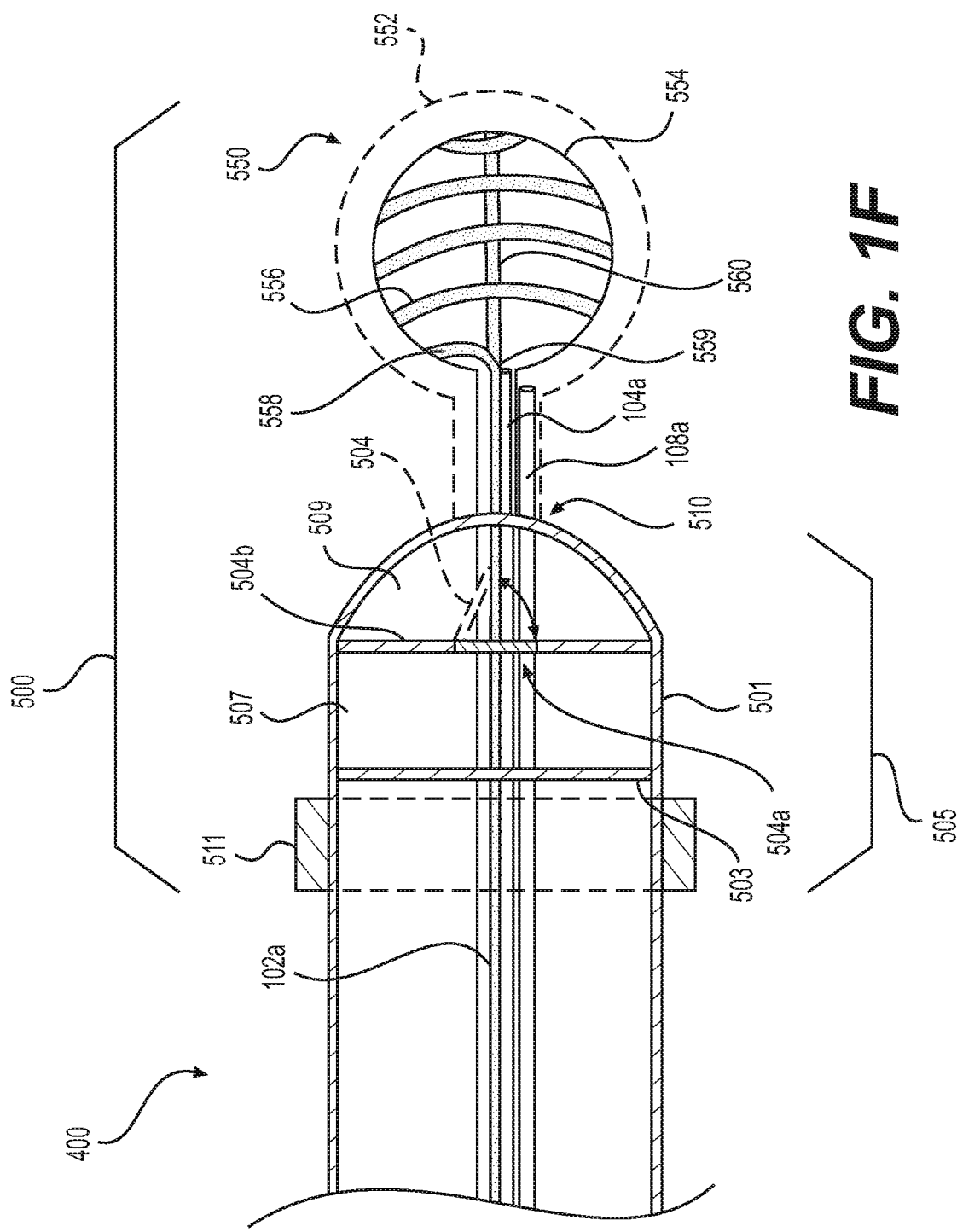
FIG. 1F is an embodiment of an applicator extender in conjunction with an embodiment of a treatment balloon that can be fitted in association with the distal end portion of the embodiment of the catheter of FIG. 1E, or that can be fitted in association with the distal end portion of the embodiment of the catheter of FIG. 1A.

Referring now to FIG. 1F, there is illustrated the catheter 400 with an embodiment of the applicator extender balloon assembly 500 that includes an embodiment of the applicator extender 505 and an embodiment of the secondary treatment balloon 550 associated with the catheter 400 and with the various lumens of FIG. 1E, in greater detail. In the embodiment of the applicator extender balloon assembly 500 of FIG. 1F, the applicator extender 505 and the secondary treatment balloon 550 are integrally formed or are joined together with each other at 510, such as by being suitably joined together by suitable processes and methods, such as with a suitable adhesive, glue or tape, for example. In the embodiment of applicator extender balloon assembly 500, the applicator extender 505 can be suitably joined to the catheter 400 by a suitable locking mechanism or connector, such as the luer lock 511, or can be integrally formed or are joined together with the catheter 400, such as by being suitably joined together by suitable processes and methods, such as with a suitable adhesive, glue or tape, for example.

The applicator extender 505 in FIG. 1F, also includes a lower or proximal chamber 507 and a distal or upper chamber 509 that can receive a radioactive or other therapeutic treatment medium or a contrast medium, such as through the central lumen 102*a*, for example. The applicator extender 505 can include a base 503, as can be a suitable membrane or a suitable material as can be configured to allow passage of one or more lumens, and an outer wall 501 that can form respective portions of the lower chamber 507 and the upper chamber 509 and that can be communicatively connected to the connector or locking mechanism 511 or that can be otherwise communicatively connected to the catheter 400, as described. The lower chamber 507 and the upper chamber 509 each can selectively include a suitable fluid medium or a treatment agent, such as a radioactive fluid or a contrast agent, as can be used for mapping a position or for treatment, as can be selectively introduced though the central lumen 102*a*, for example.

The applicator extender 505 also includes an aperture 504*a* that can be selectively opened or closed by a gate member 504 that can be either adapted to be perforated or that can be adapted to be selectively opened or closed by passage or removal of the central lumen 102*a* or of an extension thereof in the applicator extender 505, as described, and/or by the lumens 104*a* and 108*a* or an extension thereof in the applicator extender 505, as described. The gate member 504 can be formed in or as a part of a separation wall 504*b*, formed between the lower chamber 507 and the upper chamber 509, as can be formed of silicone or a rubber type material, or other suitable material, or can be a membrane of a suitable material, for example.

As described in relation to FIG. 1E, the lumens 104*a* and 108*a* can be extended through the applicator extender 505, such as by a suitable connector lumen in the applicator extender 505, to be placed in communication with the secondary treatment balloon 550. The lumen 104*a* in is communication with the inner secondary treatment balloon 554 and the lumen 108*a* is in communication with the outer secondary treatment balloon 552 to respectively selectively inflate and deflate the inner secondary treatment balloon 554 and the outer secondary treatment balloon 552 to position and/or stabilize the secondary treatment balloon 550, the outer secondary treatment balloon 552/the inner secondary treatment balloon 554, in a body cavity to be treated.

Similarly, the lumens 104*a* and 108*a* can receive and remove a fluid medium, as previously described, such as saline solution or a gaseous medium, such as by a syringe or other suitable delivery mechanism, such as a pump, to selectively inflate and deflate the inner secondary treatment balloon 554 and the outer secondary treatment balloon 552, to provide a corresponding balloon, shape, size and configuration in the body cavity for the treatment, for example.

The inner secondary treatment balloon 554 has at least one or both of a first secondary treatment lumen 556 and a second secondary treatment lumen 560. The first secondary treatment lumen 556 can be positioned in association with the periphery of the inner secondary treatment balloon 554 and can be integrally formed with or affixed to or otherwise positioned in conjunction with the inner secondary treatment balloon 554, such as by a suitable glue or adhesive, for example. The first secondary treatment lumen 556 can be positioned in association with the periphery of the inner secondary treatment balloon 554, such as either in association with an interior surface or in association with an exterior surface of the inner secondary treatment balloon 554, desirably in a generally spiral type configuration, such as illustrated in FIG. 1F, for example. The first secondary treatment lumen 556 is communicatively connected to the central lumen 102a or an extension thereof in the applicator extender balloon assembly 500 by a connector or connector portion 558 to deliver a radioactive dose or other therapeutic treatment through the central lumen 102a to a treatment site in a cavity, such as by insertion of the radioactive wire 107 or providing a therapeutic agent through the central lumen 102a, the connector 558 and the first secondary treatment lumen 556, for example.

In the inner secondary treatment balloon 554, the second secondary treatment lumen 560 can be integrally formed with or affixed to or otherwise positioned in conjunction with the inner secondary treatment balloon 554, such as by a suitable glue or adhesive, for example. The second secondary treatment lumen 560 is communicatively connected to the central lumen 102a by a connector or connector portion 559 to deliver a radioactive dose or other therapeutic treatment through the central lumen 102a to a treatment site in a cavity, such as by insertion of the radioactive wire 107 or providing a therapeutic agent through the central lumen 102a, the connector 559 and the second secondary treatment lumen 560, for example. The second secondary treatment lumen 560 is desirably formed in an interior portion of the inner secondary treatment balloon 554 desirably extending in a generally longitudinal direction in a generally central portion of the inner secondary treatment balloon 554, for example.

Figure 1G:
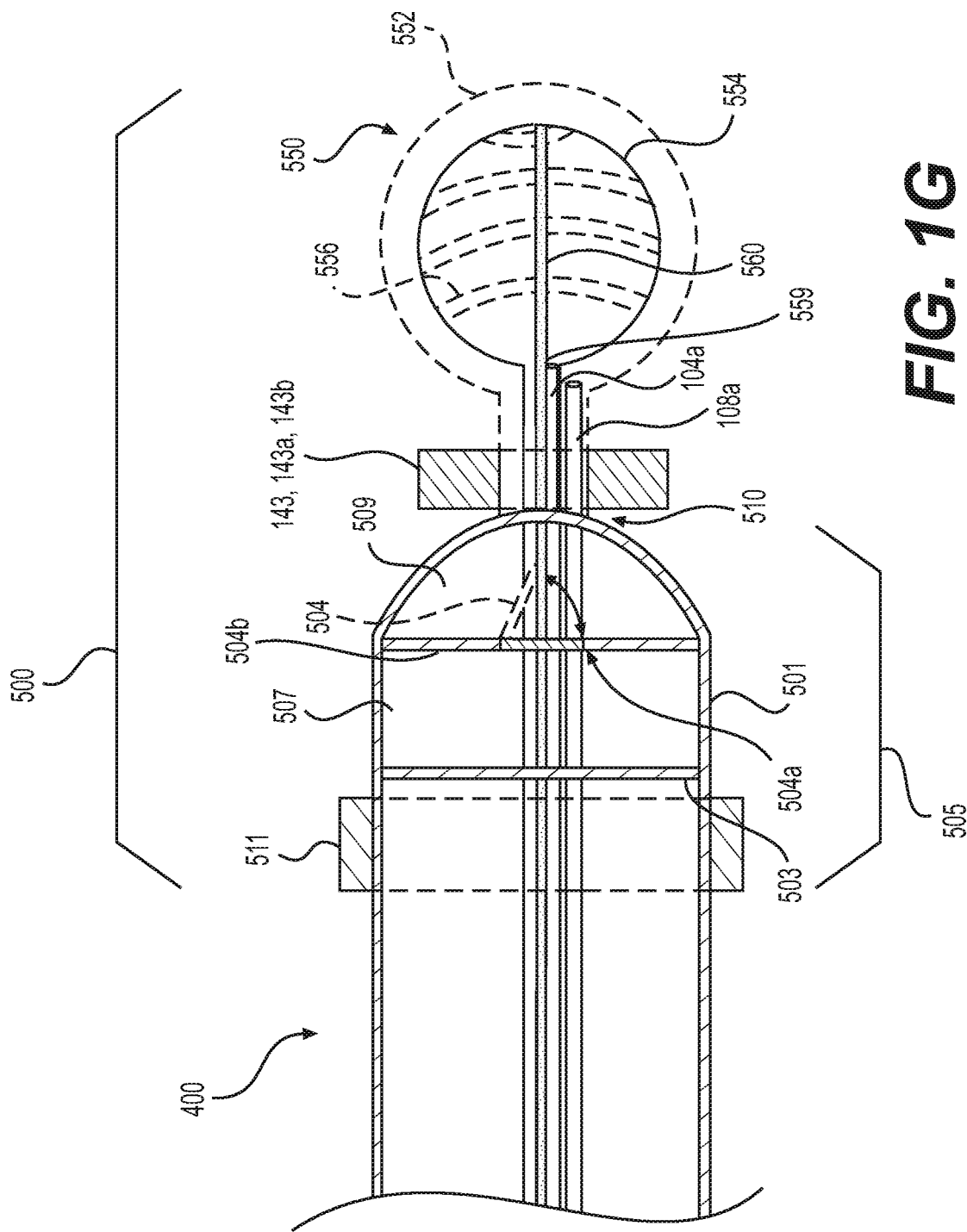
FIG. 1G is another embodiment of an applicator extender in conjunction with an embodiment of a treatment balloon that can be fitted in association with the distal end portion of the embodiment of the catheter of FIG. 1E, or that can be fitted in association with the distal end portion of the embodiment of the catheter of FIG. 1A.

Referring now to FIG. 1G, there is illustrated the catheter 400 with an embodiment of the applicator extender balloon assembly 500 that includes an embodiment of the applicator extender 505 and an embodiment of the secondary treatment balloon 550 associated with the catheter 400 and with the various lumens of FIG. 1E, in greater detail. The applicator extender balloon assembly 500 in association with the catheter 400 in FIG. 1G has similar components and structure to that described with respect to the applicator extender balloon assembly 500 illustrated in FIG. 1F. However, in the applicator extender balloon assembly 500 of FIG. 1G, there is included a connector or locking mechanism 143, such as a suitable luer lock, that can include suitable male or female connectors 143a and 143b to connect the applicator extender 505 and the secondary treatment balloon 550 for a treatment. Also, in the applicator extender balloon assembly 500 of FIG. 1G the inner secondary treatment balloon 554 can only include, for example, the second secondary treatment lumen 560 and the connector 559, with the first secondary treatment lumen 556 being optionally indicated by the dashed lines and the connector 558 (illustrated in FIG. 1F) not being shown in FIG. 1G.

Figure 1H:
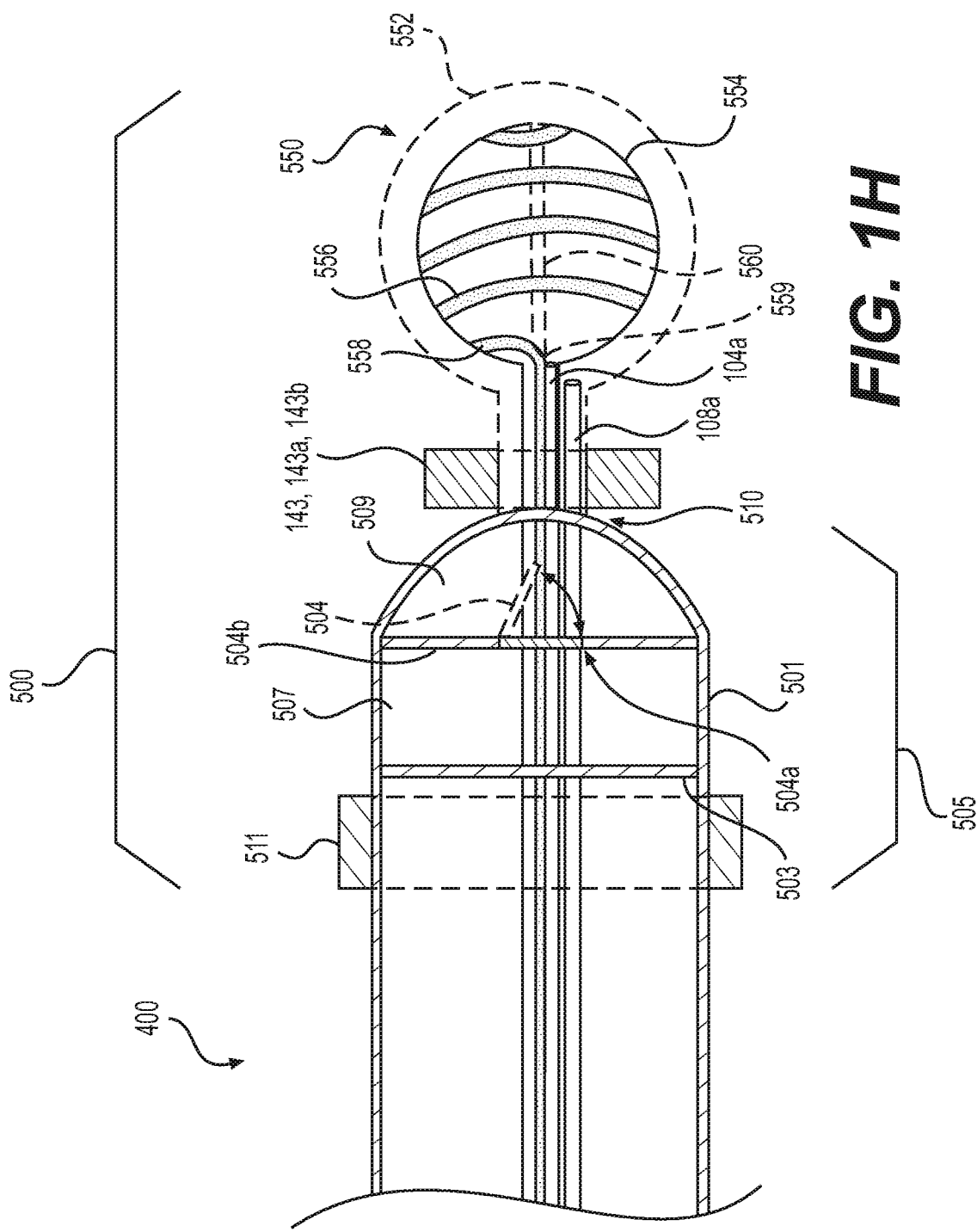
FIG. 1H is a further embodiment of an applicator extender in conjunction with an embodiment of a treatment balloon that can be fitted in association with the distal end portion of the embodiment of the catheter of FIG. 1E, or that can be fitted in association with the distal end portion of the embodiment of the catheter of FIG. 1A.

Referring now to FIG. 1H, there is illustrated the catheter 400 with an embodiment of the applicator extender balloon assembly 500 that includes an embodiment of the applicator extender 505 and an embodiment of the secondary treatment balloon 550 associated with the catheter 400 and with the various lumens of FIG. 1E, in greater detail. The applicator extender balloon assembly 500 in association with the catheter 400 in FIG. 1H has similar components and structure to that described with respect to the applicator extender balloon assembly 500 illustrated in FIG. 1F. However, in the applicator extender balloon assembly 500 of FIG. 1H, there is included a connector or locking mechanism 143, such as a suitable luer lock, that can include suitable male or female connectors 143a and 143b to connect the applicator extender 505 and the secondary treatment balloon 550 for a treatment. Also, in the applicator extender balloon assembly 500 of FIG. 1H the inner secondary treatment balloon 554 can only include, for example, the first secondary treatment lumen 556 and the connector 558, with the second secondary treatment lumen 560 and the connector 559 being optionally indicated by the dashed lines.

Figure 1I:
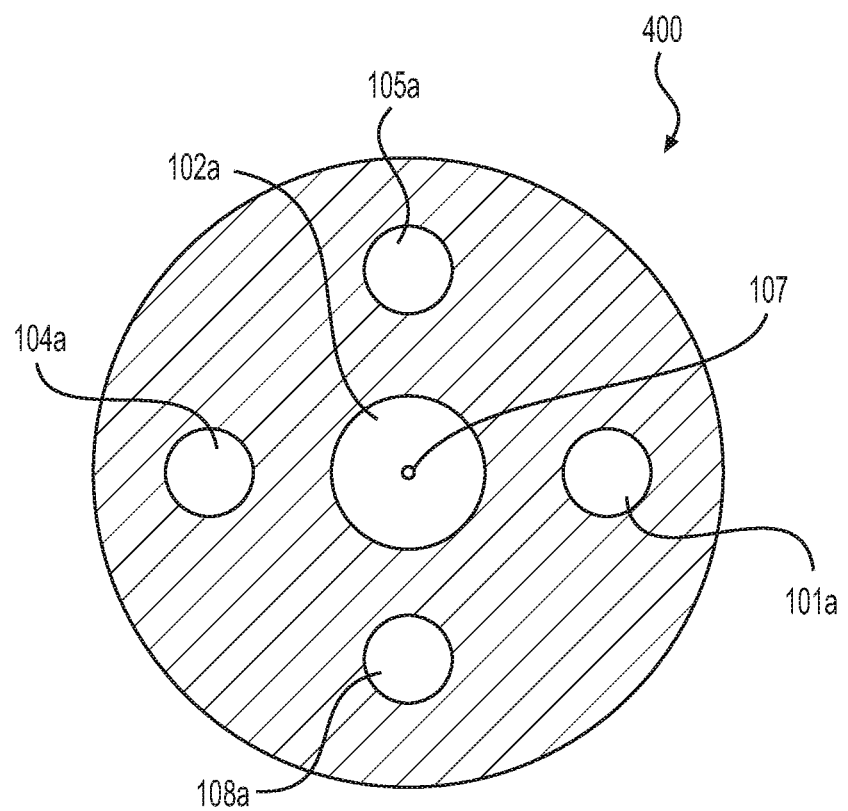
FIG. 1I is a cross-sectional view taken along lines 1I-1I of the embodiment of the catheter of FIG. 1E.

Referring to FIG. 1I, there is illustrated is a cross sectional planar view taken along the 1I-1I plane of the catheter 400 of FIG. 1E. The catheter 400 is illustrated in section in FIG. 1I along with relative positions of the lumens 101a, 102a, 104a, 105a and 108a, for example. Also, FIG. 1I illustrates a relative position of the radioactive wire 107 within the lumen 102a. The central lumen 102a allows for selectively inserting and positioning the radioactive wire, such as the radioactive wire 107, or other suitable treatment medium, for delivery of a treatment, for example.

The catheters 100, 300 and 400, and the various balloons and components thereof including the applicator extender balloon assembly 500 and components thereof can be made of various suitable materials, including, for example, nylon, polyurethane, Polyether block amide Pebax®, poly(ethylene terephthalate), commonly abbreviated PET or other thermoplastic elastomers. Nylon can be desirably used, since it can be fused together with the catheter, for example.

Figure 2A:
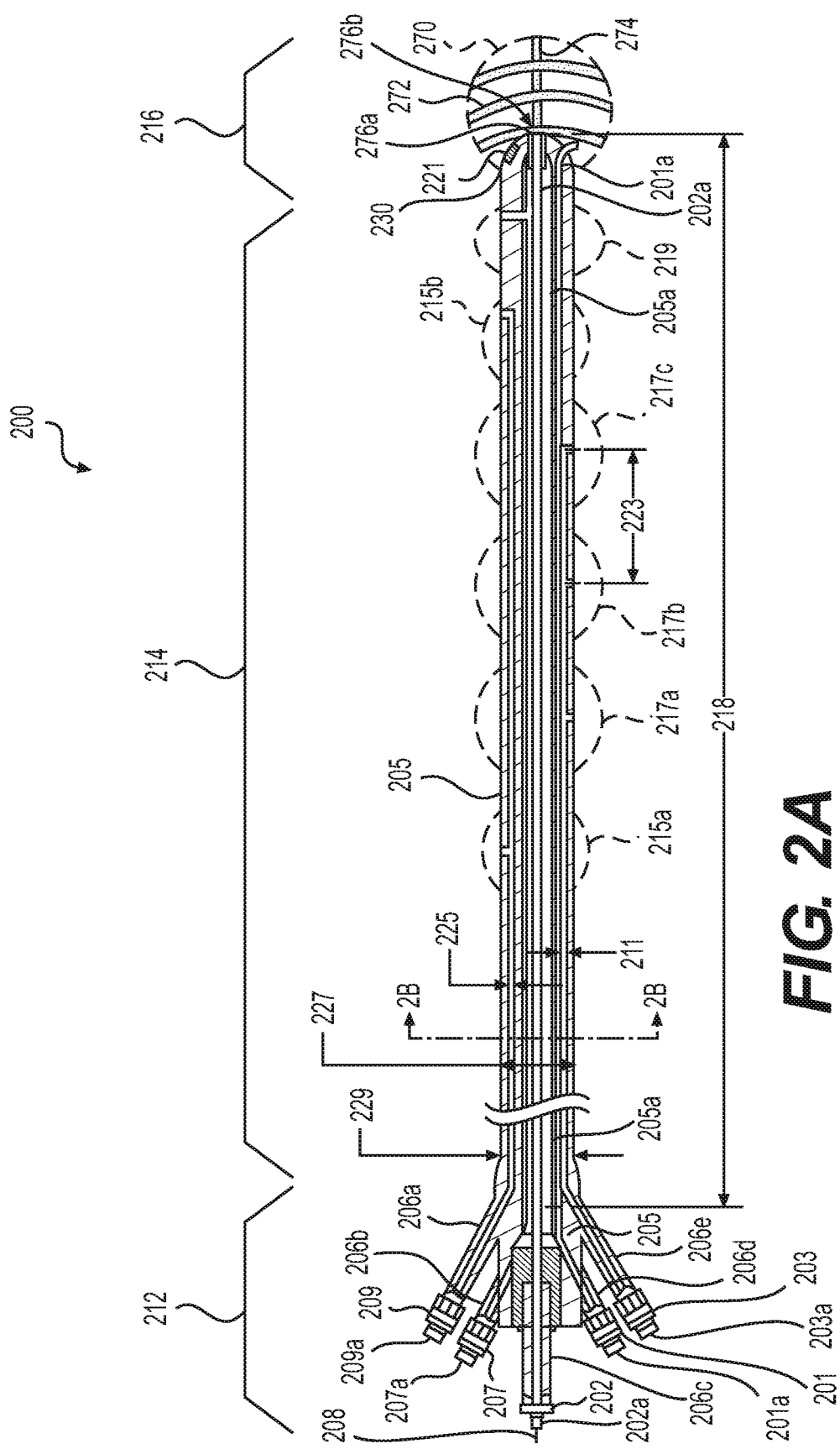
FIG. 2A is a longitudinal plan view of an embodiment of a multi-purpose balloon catheter according to the present invention.

Referring now to FIG. 2A, there is provided a multi-purpose balloon single intra-cavity catheter 200 having a plurality of various sized balloons that may be arranged in a plurality of independent and distant balloons groups, and can enable fixing, stabilizing or positioning of radioactive material, such as radioactive wires, in a cavity, such as in the esophagus or in other organs or in bodily or surgically created cavities, to deliver a radiation dose or other therapeutic agent to a targeted portion of the body for treatment. Moreover, the catheter 200 can allow for diagnosing the anatomy of abnormal organ shape by evaluating the balloon shape (with contrast agent) by comparing to shapes of normal healthy patient organs, for example.

FIG. 2A shows an embodiment of the catheter 200, similar to the structure of the catheter 100 of FIG. 1A fitted with a secondary treatment balloon 270 as shown in FIG. 2A that is adapted to receive a radioactive wire that encircles or is arranged in association with an inner portion of the balloon for delivering a relatively higher dose of radiation and to position the balloon in the cavity or organ for treatment. The balloon attached to the catheter 200 can include outer and inner balloons to position and deliver the treatment. The outer balloon can also assist in protecting the inner balloon that is adapted to receive the radioactive material, such as a radioactive wire, or a therapeutic agent for treatment, as to be further described.

Referring now to the drawings in greater detail, there is illustrated in FIG. 2A an embodiment of the multi-purpose balloon single intra-cavity catheter 200 according to the teachings of the invention. The multi-purpose balloon single intra-cavity catheter 200 includes a proximal end portion 212, a central portion 214 as can have a generally tubular shaped body 205, and a non-branching distal end portion 216, with the non-branching distal end portion 216 including a suitable marker such as an X-ray marker 221 to indicate a position of the non-branching distal end portion 216 of the catheter 200. The X-ray marker 221 typically can be gold, lead, tungsten or other heavy metal suitable for X-ray visualization, or can be other suitable material, as can depend on the use or application, and should not be construed in a limiting sense.

The multi-purpose balloon single intra-cavity catheter 200 can be made of various suitable materials, such as a polymeric material, such as polyurethane or polyacrylic, among other examples, as can depend on the use or application, for example. Typically, a length 218 of the multi-purpose balloon single intra-cavity catheter 200 of FIG. 2A is about 78 cm to the tip area from the base area of the multi-purpose balloon single intra-cavity catheter 200, but the catheter 200 can be of various suitable lengths and dimensions, as can depend on the use or application, for example. A diameter 229 of the central portion 214 of the catheter 200 of FIG. 2A is typically 0.45 cm, but can be of various suitable diameters, as can depend on the use or application, for example.

The proximal end portion 212 of the catheter 200 includes the plurality of neck portions 206a, 206b, 206c, 206d and 206e, made of similar suitable material as the catheter 200. The neck portions 206a, 206b, 206c, 206d and 206e each include a corresponding lumen 201a, 202a, 203a, 207a and 209a therein that extends from the proximal end portion 212, such as within the catheter 200, for balloon inflation or for treatment delivery, for example. The neck portions 206a, 206b, 206c, 206d and 206e and corresponding lumens 201a, 202a, 203a, 207a and 209a are desirably associated with a corresponding suitable connector or connecting mechanism 201, 202, 203, 207 and 209, such as suitable luer locks 201, 202, 203, 207 and 209, that can be a male or a female connection, for example.

For example, the luer-locks 203, 207 and 209 can be fitted with syringes for selectively inflating balloons 215a, 215b, balloons 217a, 217b, and 217c and balloon 219 to a predetermined size, for a particular use or application, for example. The balloons 215a, 215b, the balloons 217a, 217b, and 217c and the balloon 219 being desirably located in association with the central portion 214 to facilitate positioning and/or stabilizing the catheter 200 for delivery of a treatment. In the catheter 200, the lumen 203a associated with the luer lock 203 can receive and remove a fluid medium, such as saline solution or a gaseous medium, such as by a syringe or other suitable delivery mechanism, such as a pump, to selectively inflate and deflate the balloons 217a, 217b, and 217c, for example.

Also, the lumen 207a associated with the luer lock 207 can receive and remove a fluid medium, such as satin solution or a gaseous medium, such as a syringe or other suitable delivery mechanism, such as a pump, to selectively inflate or deflate the balloon 219, for example. Similarly, the lumen 209a associated with the luer lock 209 can receive and remove a fluid medium, such as saline solution or a gaseous medium, such as a syringe or other suitable deliver mechanism, such as a pump, to selectively inflate or deflate the balloons 215i a and 215b, for example. The locking mechanism or connector, such as provided by the luer locks 203, 207 and 209, when affixed to the catheter 200 can provide for selectively not allowing or selectively allowing a fluid medium, such as including fluids, fluid or gaseous mediums, or air, or allowing a contrast medium, for example, to pass through a corresponding connecting point provided by the connector or connecting mechanism 203, 207, and 209, such as luer locks, with the catheter 200. As illustrated in FIG. 2A, the balloons 215a, 215b, 217a, 217b, 217c and 219 can be arranged in a plurality of independent and distinct balloon groups in association with the central portion 214 of the catheter 200. For example, as illustrated from FIG. 2A, the balloons 215a and 215b can form a first independent and distinct balloon group, the balloons 217a, 217b and 217c can form a second independent and distinct balloon group, and the balloon 219 can form a third independent and distinct balloon group. Each independent and distinct balloon group can be selectively inflated or deflated or can also receive or have removed a contrast liquid or other contrast medium independently of they balloons of another independent and distinct balloon group, such as through corresponding ones of the plurality of connectors, such as connectors 203, 207, and 209, and through the associated corresponding ones of the plurality of the lumens, such as lumens 203a, 207a and 209a, for example.

As depicted in FIG. 2A, the central lumen 202a associated with the connector 202, such as a luer lock, can be used to insert a radioactive wire 208 or a radioactive seed, for example, as a radiation source for treatment at a specific or predetermined site or location of or within the organ or other cavity, into the catheter 200. Also, the central lumen 202a associated with the locking mechanism or connector 202, such as a luer lock, can be used with suction or a syringe to remove bodily fluids or material from a cavity in a body using the treatment catheter 200, for example. The central lumen 202a can be positioned in a larger main lumen 205a extending through the Catheter 200, as illustrated in FIG. 2A. The locking mechanism or connector 202 for the central lumen 202a can allow medical personnel to have a relatively easier controlled delivery and guidance for treatment and extraction within a treatment area, for example.

Selectively inflating the balloons 215a, 215b, 217a, 217b, 217c and 219 can allow for selectively positioning and stabilizing the catheter 200 for administration of a therapeutic treatment or for removal bodily fluids or material in or within a cavity, such as in a bodily organ or in a cavity region, such as in or within the esophagus, rectum, stomach or a surgically created cavity, such as in or within the breast, another organ or bodily tissue, such as through the lumen 202a, for example. The lumens 203a, 207a and 209a and the inflated balloons 215a, 215b, 217a, 217b, 217c and 219 can contain a contrast liquid or other contrast medium, such as for contrast purposes in imaging applications, as can also be used for inflation and deflation of the balloons 215a, 215b, 217a, 217b, 217c and 219, for positioning, stabilization and/or treatment, for example.

As discussed herein, the catheter 200 includes a plurality of balloons, such as the balloons 215a, 215b, 217a, 217b, 217c and 219 arranged in a plurality of independent and distinct balloon groups, such as the first balloon group including balloons 215a and 215b, the second balloon group including balloons 217a, 217b, 217c, and the third balloon Group including balloon 219. The lumens of the catheter 200, such as the lumens 203a, 207a and 209a, can be communicatively connected to a single or to any of various pluralities of balloons. For example, the lumen 203a can be connected with balloons 217a, 217b, 217c of the second balloon group, the lumen 207a can be connected to the balloon 219 of the third balloon group, and the lumen 209a can be connected to balloons 215a and 215b of the first balloon group, as illustrated in FIG. 2A, for example. Also, the catheter 200 ran have any of various other suitable connection arrangements with more or less lumens or balloons, as Can depend on the use or application, for example.

Further, the balloons, such as the balloons 215a, 215b, 217a, 217b, 217c and 219, can have any of various suitable sizes or shapes, such as cylindrical, spherical, oval, oblong, toroidal, or other suitable shapes, as can depend on the use or application, for example. In the catheter 200, the first independent and distinct balloon group including balloons 215a and 215b, the second independent and distinct balloon group including balloons 217a, 217b and 217c, and the third independent and distinct balloon group including balloon 219 each can be of different size or shape from the balloons of the other groups, for example, as can assist in positioning and Stabilizing the catheter 200 in a cavity, such as in an organ, a body cavity or surgically created cavity, for treatment delivery.

The lumens, such as the lumens 201a, 202a, 203a, 207a and 209a, can have any of various suitable sizes, shapes or configurations, such as cylindrical, rectangular, oval, or other suitable shapes or configurations, as can depend on the use or application, for example. Also, a typical dimension of a diameter of the lumens, such as indicated at 211 for diameter of the lumen 203a and as indicated at 225 for a diameter of the lumen 209a, for inflating the corresponding balloons 215a, 215b, 217a, 217b, 217c and 219 can be typically in a range of from about 0.8 mm to about 1.5 mm, for example, but can be of various suitable dimensions, as can depend on the use or application, and should not be construed in a limiting sense.

Further, the spacing between each of the centers of adjacent ones of the balloons 217a, 217b and 217c as can desirably correspond to the spacing between adjacent exit points of the lumen 203a, can be a same or a different spacing, as can depend on the use or application, such as desirably being spaced apart by about 2.5 cm from each other as indicated at 223, for example. Also, the spacing between each of adjacent balloons of the catheter 200, such as the balloons 215a, 215b, 217a, 217b, 217c and 219, can be same or different for each pair of adjacent balloons of the catheter 200, as can depend on the use or application, for example. The first balloon group including the balloons 215a and 215b, the second balloon group including the balloons 217a, 217b and 217c, and the third balloon group including the balloon 219 are each independently arranged from each other balloon group on the catheter 200 along the length 218 of the catheter 200, such as illustrated in FIG. 2A. Also, the lumens, such as the lumens 201a, 202a, 203a, 207a, and 209a, can be positioned within the interior of the catheter 200, such interior of the catheter 200 being indicated by the numeral 227, or can be positioned or formed on or in an exterior surface or layer of the catheter 200, for example, as can depend on the use or application, for example.

The balloons, such as the balloons 215a, 215b, 217a, 217b, 217c and 219 can be made of nylon, polyurethane, Polyether block amide Pebax®, poly(ethylene terephthalate) commonly abbreviated PET, or other thermoplastic elastomers or other suitable materials, as can depend on the use or application, for example. Additionally, one or more of the balloons 215a, 215b, 217a, 217b, 217c and 219 and all of, part of or a portion of the catheter 200, such as including the body 205 of the central portion 214 of the catheter 200, can be coated or impregnated with various suitable coatings for ease of assembly such as a silicone type coating, or the balloons, such as the balloons 215a, 215b, 217a, 217b, 217c and 219, and/or the catheter, such as the catheter 200, can be impregnated or coated with various suitable therapeutic or medicinal agents for treatment at a site within the body, such as by elution of the agent from the balloon or the catheter, for example.

In an embodiment, all of, a part of or a portion of the catheter 200, as well as one or more of the balloons associated with the catheter 200, such as the balloons 215a, 215b, 217a, 217b, 217c and 219, can be uncoated or can be coated with a lubricant for lubrication for ease of positioning the catheter 200 at a treatment site, or can be coated or formed with antimicrobial or medicinal agents for delivery of a therapeutic treatment at the treatment site, for example. In this regard, in various embodiments of catheters, such as the catheter 200, various therapeutic drugs or agents can be coated onto the surface of one or more of the balloons, such as the balloons 215a, 215b, 217a, 217b, 217c and 219, or coated onto the surface of all of, part of or a portion of the catheter, such as the catheter 200, for releasing the therapeutic drug or agent internally to a specific location of the cavity being treated.

The catheter 200 of FIG. 2A having a plurality of connectors or locking mechanisms 201, 202, 203, 207 and 209, such as the luer-locks as examples of connectors or locking mechanisms, and a plurality of balloons, such as the balloons 215a, 215b, 217a, 217b, 217c and 219, can be inserted into various body cavities, such as the esophagus, but is not limited thereto and can also be inserted for treatment into other cavities, such as the rectum, vagina, etc., or surgically created cavities, wherein the radioactive wire, or other radioactive or therapeutic material or other therapeutic agent, can provide the requisite radiation dose or therapeutic treatment to treat cancerous growth or other medical conditions. Typically, the dimension of the radioactive wire, such as the radioactive wire 208, that can be inserted into the central lumen 202a, is desirably in a range of about 0.5 mm to about 0.8 mm, for example, but can be of various suitable dimensions and configurations as can depend on the use or application.

Desirably, the radioactive wire, such as the radioactive wire 208, is made of a suitable radioactive material, such as can include Iridium-192, Cobalt 60 and Yttrium 168, for example. The high dose rate (HDR) treatment delivered through the catheter, such as the catheter 200, can be conducted with Ir-192, Au-198, I-125 and Cs-131, for example. Typically, the dose of radiation delivered by the radioactive wire, such as the radioactive wire 208, is about 1 Curie to about 10 Curies per seed, but can be any suitable dose, as can depend on the use or application.

Also, HDR afterloaders can be used in conjunction with embodiments of the catheters, such as the catheter 200, for delivery of a radiation dose for treatment, such as Varisource, Gamma Med and BEBIG afterloaders or other suitable afterloaders, for example. For a low dose rate (LDR) application delivered through embodiments of catheters, such as the catheter 200, Sr-90 can be used in conjunction with the radiation wire, such as the radioactive wire 208, as well as Cs-131 and Yb-168 can be used as the radiation source, for example. Typically, the dose of radiation using the LDR configuration is usually one thousand times less than the HDR applications, such LDR does being in a range of about 1 milli Curie to about 10 milli Curies, for example.

An advantage, among others, of embodiments of catheters, such as the catheter 200, is that it can allow for delivering the radiation dose or other therapeutic agent to a specific site or a predetermined location of the organ or body cavity, such as by the radioactive wire 208, through the central lumen 202a, and can also allow, at the same time or at different times, removal of fluid or bodily material, from the area of the treatment site, such as through the central lumen 202a or through a main lumen 205a that includes the central lumen 202a, for example, as well as also providing enhanced stabilization and/or positioning of the catheter, such as the catheter 200, for treatment, by selective inflation or deflation of the corresponding balloons, such as the balloons 215a, 215b, 217a, 217b, 217c and 219, for example, as can allow selectively controlling the size of each balloon independently or in conjunction with one or more other balloons, to selectively adjust the location and positioning of the catheter at the treatment site.

Also, the catheter 200 includes, such as illustrated in FIG. 2A, an embodiment of a secondary treatment balloon 270 at the distal end portion 216 of the catheter 200. The secondary treatment balloon 270 can be selectively inflated or deflated to be positioned in a body cavity or a surgically created cavity for delivery of a radiation dose or other treatment agent to the surrounding tissue. In the catheter 200, the lumen 201*a* associated with a connector or locking mechanism 201, such as a suitable luer lock, can receive and remove a fluid medium, such as saline solution or a gaseous medium, such as by a syringe or other suitable delivery mechanism, such as a pump, to selectively inflate or deflate the secondary treatment balloon 270, for example.

In the embodiment of the catheter 200, the secondary treatment balloon 270 can be integrally formed with or affixed to or otherwise positioned in conjunction with the catheter 200, such as by a suitable glue or adhesive, for example, as indicated at attachment area 230. The secondary treatment balloon 270 has at least one or both of a first secondary treatment lumen 272 and a second secondary treatment lumen 274. The first secondary treatment lumen 272 can be positioned in association with the periphery of the secondary treatment balloon 270, such as illustrated in FIG. 2A, for example, and can be integrally formed with or affixed to or otherwise positioned in conjunction with the secondary treatment balloon 270, such as by a suitable glue or adhesive, for example.

The first secondary treatment lumen 272 is desirably of a generally spiral type configuration, for example, as illustrated in FIG. 2A. The first secondary treatment lumen 272 can be positioned in association with the periphery of the secondary treatment balloon 270, such as either on an interior surface or on an exterior surface of the secondary treatment balloon 270, for example, but desirably is placed in association with an interior surface or portion thereof The first secondary treatment lumen 272 is communicatively connected to the central lumen 202*a* by a connector or connector portion 276*a* or can be integrally formed therewith to deliver a radioactive dose or other therapeutic treatment agent through the central lumen 202*a* and through the first secondary treatment lumen 272 to a treatment site in a cavity, such as by insertion of the radioactive wire 208 or providing a therapeutic agent through the central lumen 202*a*, the connector 276*a* and the first secondary treatment lumen 272, for example.

The second secondary treatment lumen 274 is also communicatively connected to the central lumen 202*a* by a connector or connector portion 276*b*, or can be integrally formed therewith to deliver a radioactive dose or other therapeutic treatment agent through the central lumen 202*a* and through the second secondary treatment lumen 274 to a treatment site in a cavity, such as by insertion of the radioactive wire 208 or providing a therapeutic agent through the central lumen 202*a*, the connector 276*b* and the second secondary treatment lumen 274, for example. The second secondary treatment lumen 274 is desirably formed in an interior portion of the secondary treatment balloon 270 desirably extending in a generally longitudinal direction in a generally central portion of the secondary treatment balloon 270, for example.

Figure 2B:
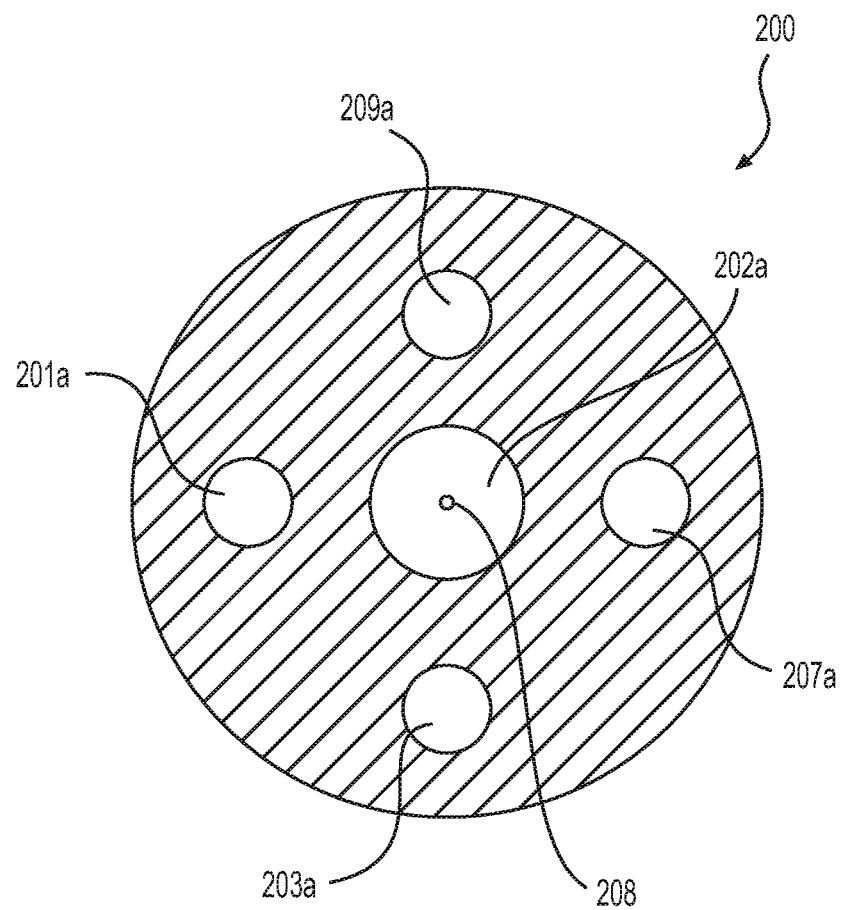
FIG. 2B is a cross-sectional view taken along lines 2B-2B of FIG. 2A.

FIG. 2B shows the cross sectional view taken along the 2B-2B plane of the catheter 200 of FIG. 2A. The catheter 200 is illustrated in section in FIG. 2B along with relative positions of the lumens 201*a*, 202*a*, 203*a*, 207*a* and 209*a*, for example. Also, FIG. 2B illustrates a relative position of the radioactive wire 208 within the central lumen 202*a*. The central lumen 202*a* allows for selectively inserting and positioning the radioactive wire, such as the radioactive wire 208, or other suitable treatment medium, for delivery of a treatment, for example.

Figure 2C:
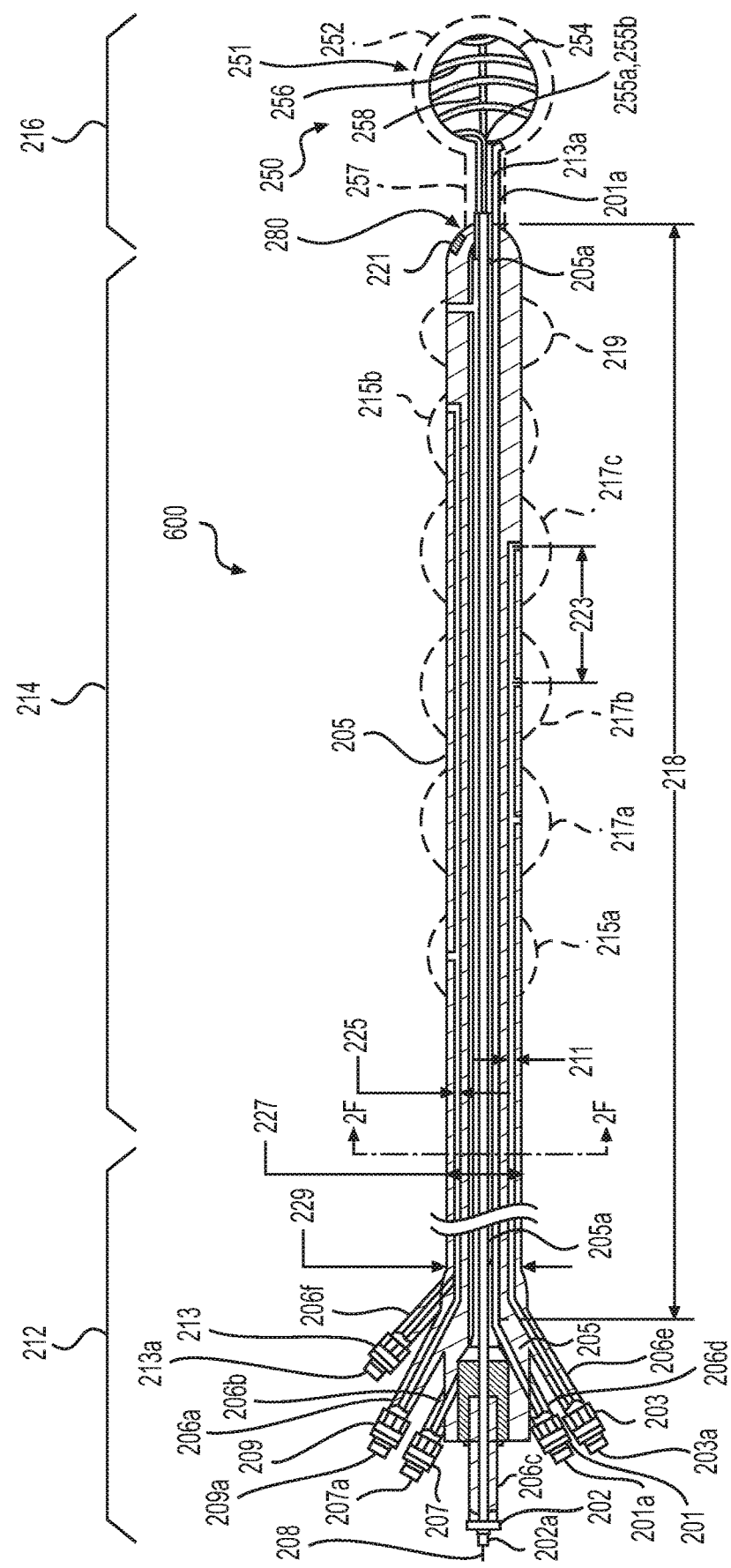
FIG. 2C is a plan view of another embodiment of a multi-purpose balloon catheter fitted with a treatment balloon in association with the distal end portion of the catheter, the treatment balloon having a spiral lumen or a longitudinal lumen adapted to receive a radioactive wire or a radioactive material.

Referring now to FIG. 2C, another embodiment of a catheter 600 is illustrated. The catheter 600 is similar to the catheter 200 of FIG. 2A as to components and structure, as described, including the balloons 215*a*, 215*b*, 217*a*, 217*b*, 217*c* and 219, and the corresponding lumens 201*a*, 202*a*, 203*a*, 207*a* and 209*a* with the connectors or locking mechanisms 201, 202, 203, 207 and 209, as described, and can be of suitable shapes, dimensions and materials, as described in relation to the catheter 200. However, the catheter 600 also includes an additional connector or locking mechanism 213, such as a suitable luer lock, that connects to a neck portion 206*f* of the catheter 600 associated with an additional lumen 213*a*, with the additional lumen 213*a* and the lumen 201*a* associated with an embodiment of a secondary treatment balloon assembly 250 at the distal end portion 216 of the catheter 600 that is illustrated in greater detail and further described herein in relation to FIGS. 2D and 2E.

Figure 2D:
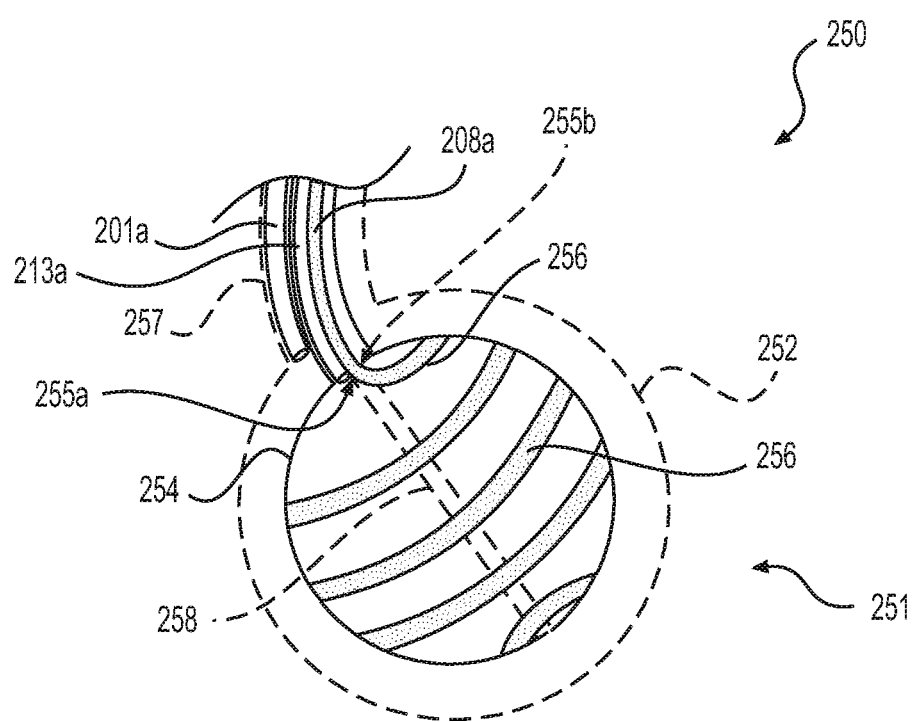
FIG. 2D is an embodiment of a treatment balloon having a spiral lumen or a longitudinal lumen adapted to receive a radioactive wire or a radioactive material as can be with the embodiment of the catheter of FIG. 2C.

Referring to FIGS. 2C and 2D, in the embodiment of the catheter 600, the secondary treatment balloon assembly 250 can be integrally formed with or affixed to or otherwise positioned in conjunction with the catheter 600, such as by a suitable glue or adhesive, for example, as indicated at attachment area 280. The secondary treatment balloon assembly 250 includes a secondary treatment balloon 251 that includes an outer secondary treatment balloon 252 and an inner secondary treatment balloon 254.

The outer secondary treatment balloon 252 and the inner secondary treatment balloon 254 can be selectively inflated or deflated to be positioned in a body cavity or a surgically created cavity to be treated, for example. The lumen 213*a* is in communication with the inner secondary treatment balloon 254 and the lumen 201*a* is in communication with the outer secondary treatment balloon 252 to respectively selectively inflate or deflate the inner secondary treatment balloon 254 and the outer secondary treatment balloon 252 to position and/or stabilize the secondary treatment balloon 251, including the inner secondary treatment balloon 254/ the outer secondary treatment balloon 252, in a body cavity or surgically created cavity to be treated. Similarly, the lumens 201*a* and 213*a* can receive or can remove a fluid medium, as previously described, such as saline solution or a gaseous medium, such as by a syringe or other suitable delivery mechanism, such as a pump, to selectively inflate or deflate the inner secondary treatment balloon 254 and the outer secondary treatment balloon 252, to provide a corresponding balloon; shape, size and configuration in the body cavity for the treatment, for example.

The secondary treatment balloon 251 has at least one or both of a first secondary treatment lumen 256 and a second secondary treatment lumen 258, the second secondary treatment lumen 258 being optionally indicated in FIG. 2D. The first secondary treatment lumen 256 can be positioned in association with the periphery of the inner secondary treatment balloon 254 and can be integrally formed with or affixed to or otherwise positioned in conjunction with the inner secondary treatment balloon 254, such as by a suitable glue or adhesive, for example. The first secondary treatment lumen 256 is desirably of a generally spiral type configuration, for example, as illustrated in FIGS. 2C and 2D. The first secondary treatment lumen 256 can be positioned in association with the periphery of the inner secondary treatment balloon 254, such as either on an interior surface or on an exterior surface of the inner secondary treatment balloon 254, for example, but desirably is placed on an interior surface or portion thereof.

The first secondary treatment lumen 256 is communicatively connected to the central lumen 202a by a connector or connector portion 255a, and the central lumen 202a can extend into a neck area 257 of the secondary treatment balloon assembly 250 by a connector portion 208a as can be communicatively connected to or integrally formed with the central lumen 202a, to deliver a radioactive dose or other therapeutic treatment agent through the central lumen 202a, through the connector or connector portion 255a and through the first secondary treatment lumen 256 to a treatment site or a predetermined location in a cavity, such as by insertion of the radioactive wire 208 or providing a therapeutic agent through the central lumen 202a through the neck area 257, the connector 255a and the first secondary treatment lumen 256, for example.

In the inner secondary treatment balloon 254, the second secondary treatment lumen 258 can be integrally formed with or affixed to or otherwise positioned in conjunction with the inner secondary treatment balloon 254, such as by a suitable glue or adhesive, for example. The second secondary treatment lumen 258 is desirably formed in an interior portion of the inner secondary treatment balloon 254 desirably extending in a generally longitudinal direction in a generally central portion of the inner secondary treatment balloon 254, for example.

The second secondary treatment lumen 258 is also communicatively connected to the central lumen 202a by a connector or connector portion 255b, or can be integrally formed therewith to deliver a radioactive dose or other therapeutic treatment agent through the central lumen 202a, the connector 255b and through the second secondary treatment lumen 258 to a treatment site in a cavity, such as by insertion of the radioactive wire 208 or providing a therapeutic agent through the central lumen 202a, the connector 255b and the second secondary treatment lumen 258, for example. The central lumen 202a can extend into a neck area 257 of the secondary treatment balloon assembly 250 by the connector portion 208a as can be communicatively connected to or integrally formed with the central lumen 202a, to deliver a radioactive dose or other therapeutic treatment through the central lumen 202a to a treatment site in a cavity, such as by insertion of the radioactive wire 208 or providing a therapeutic agent through the central lumen 202a through the neck area 257, the connector 255b and the second secondary treatment lumen 258 for example.

Figure 2E:
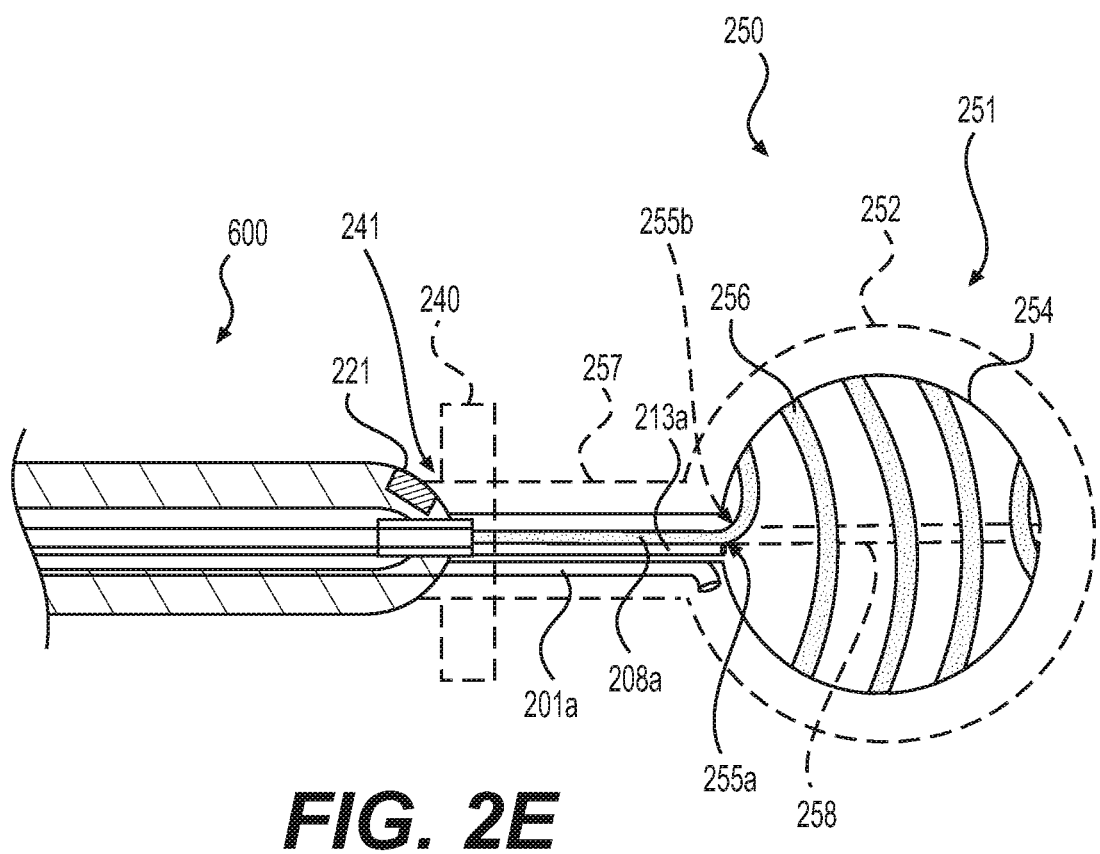
FIG. 2E another embodiment of a treatment balloon having a spiral lumen or a longitudinal lumen adapted to receive a radioactive wire or a radioactive material as can be with the embodiment of the catheter of FIG. 2C.

Referring now to FIG. 2E, there is illustrated the catheter 600 with an embodiment of the secondary treatment balloon assembly 250 that includes similar components and structure to that described with respect to the secondary treatment balloon assembly 250 illustrated in FIGS. 2C and 2D. However, in the secondary treatment balloon assembly 250 of FIG. 2E, there can be included a connector or locking mechanism 240, such as a suitable luer lock, that can include suitable male or female connectors to selectively connect the secondary treatment balloon assembly 250 to the catheter 600.

The connector or locking mechanism 240 or a portion thereof can be integrally formed with or suitably connected with the distal end portion 216 of the catheter 600 at an area 241, such as with a suitable glue or adhesive, for example. Also, the connector or locking mechanism 240 or a portion thereof can be integrally formed with or suitably connected with the proximal end of the neck area 257 of the secondary treatment balloon assembly 250 at the area 241, such as with a suitable glue or adhesive. Such connector or locking mechanism 240 can assist in enabling attaching or exchanging with the catheter 600 various sizes and configurations of the secondary treatment balloon assembly 250 at the area 241 to facilitate treatment and treatment options, for example. Further, in FIG. 2E, the inner secondary treatment balloon 254 only includes the first secondary treatment lumen 256 and the connector 255a, with the second secondary treatment lumen 258 and the connector 255b being optionally indicated by dashed lines therein.

Also, in the secondary treatment balloon assembly 250 illustrated and described with respect to FIGS. 2C, 2D and 2E, the lumens 201a, 202a and 213a can also be extended through the neck area 257 by one or more a suitable connector lumens, as can be integrally formed or joined therewith by a suitable process or method, to respectively communicate with such corresponding connector lumens in the neck area 257 as can correspondingly communicatively connect or communicatively associate the lumens 201a, 202a and 213a with the connectors 255a, 255b, the inner secondary treatment balloon 254 the outer secondary treatment balloon 252, the first secondary treatment lumen 256 and the second secondary treatment lumen 258, as described.

Figure 2F:
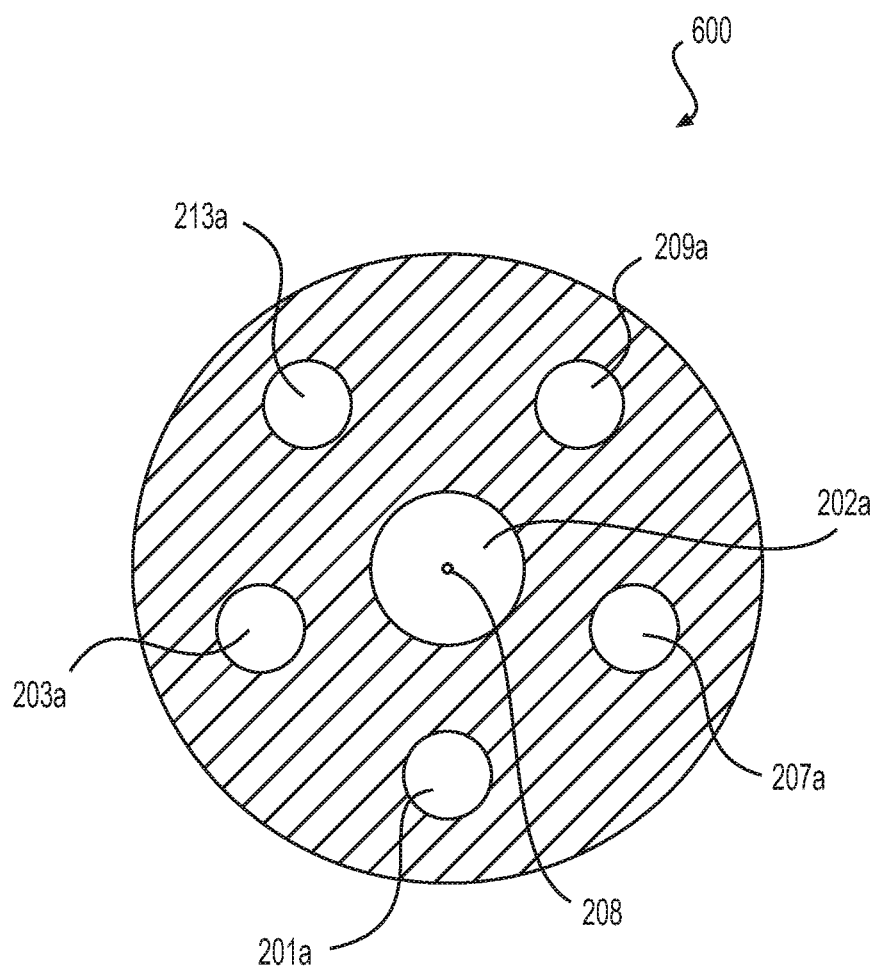
FIG. 2F is a cross-sectional view taken along lines 2F-2F of FIG. 2C.

Referring now to FIG. 2F, there is illustrated a cross sectional planar view taken along the 2F-2F plane of the catheter 600 of FIG. 2C. The catheter 600 is illustrated in section in FIG. 2F along with relative positions of the lumens 201a, 202a, 203a, 207a, 209a and 213a, for example. Also, FIG. 2F illustrates a relative position of the radioactive wire 208 within the lumen 202a. The central lumen 202a allows for selectively inserting and positioning the radioactive wire, such as the radioactive wire 208, or for selectively providing other suitable treatment mediums, for delivery of a treatment, for example.

While various embodiments of inflatable balloons of embodiments of the multi-purpose balloon catheters described herein have been associated with a single spiral or a circular treatment lumen or a single treatment lumen, or associated with first and second treatment lumens, positioned in association with a distal inflatable balloon of the catheter, embodiments of distal inflatable balloons for delivery of treatment should not be construed as so limited. In this regard, a distal inflatable balloon for treatment can include a relatively large number of treatment lumens associated with a corresponding distal inflatable balloon, such as can include one to fifteen treatment lumens associated with or attached to a distal inflatable balloon, desirably attached to or associated with an inner wall or inner surface of the balloon or attached to or associated with an inner balloon of a distal inflatable balloon, for example.

Such multiple treatment lumens associated with a distal treatment balloon can be selectively used for delivery of a plurality of treatments, procedures, or other therapeutic purposes, such as for delivery of radiation therapy, delivery of contrast agents for imaging or mapping a location, delivery of various therapeutic agents, etc., for example, using a single distal balloon associated with a catheter, similar to those described herein. For example, a distal inflatable balloon associated with a catheter for treatment or a related procedure desirably can include five such treatment lumens, such as one treatment lumen being positioned at a center of an inner treatment balloon and four treatment lumens positioned in association with the periphery of the inner treatment balloon, for example.

It is to be understood that the present invention is not limited to the embodiments described above, but encompasses any and all embodiments within the scope of the following claims.

I claim:

1. A multi-purpose intra-cavity balloon catheter for a medical treatment, comprising:
a single intra-cavity catheter configured for insertion into a body cavity for the medical treatment, the single intra-cavity catheter having a proximal end portion, a central portion and a non-branching distal end portion;
a plurality of lumens positioned in association with the single intra-cavity catheter extending from the proximal end portion of the single intra-cavity catheter, and the plurality of the lumens including a central lumen, the central lumen being positioned in communication with an extraction opening at the non-branching distal end portion of the single intra-cavity catheter, the central lumen being configured to enable removal of fluid or material received through the extraction opening from the body cavity while the single intra-cavity catheter is positioned in the body cavity for the medical treatment;
a plurality of independent and distinct balloon groups positioned in association with the central portion of the single intra-cavity catheter, each of the plurality of independent and distinct balloon groups being independently spaced from each other of the plurality of independent and distinct balloon groups on the single intra-cavity catheter, each of the plurality of independent and distinct balloon groups is positioned in a non-overlapping contiguous arrangement on a same longitudinal axis of the single intra-cavity catheter, each of the plurality of independent and distinct balloon groups including at least one inflatable balloon, and each of the plurality of independent and distinct balloons group being communicatively associated with a corresponding at least one of the plurality of lumens, wherein at least one of the plurality of independent and distinct balloon groups is configured to be selectively inflated or deflated to selectively fix or position the single intra-cavity catheter in the body cavity for the medical treatment, and
at least one other of the plurality of independent and distinct balloon groups is configured to receive a treatment medium or a contrast medium for the medical treatment.

2. The multi-purpose intra-cavity balloon catheter for a medical treatment according to claim 1, further comprising:
a plurality of connectors positioned in association with the proximal end portion of the single intra-cavity catheter, the plurality of connectors each being respectively communicatively connected with a corresponding at least one of the plurality of lumens, the plurality of connectors being configured to enable respectively selectively receiving or removing through corresponding ones of the plurality of lumens one or more of a liquid saline solution, a fluid medium, a gaseous medium, a contrast medium, a radioactive material or other treatment medium for the medical treatment.

3. The multi-purpose intra-cavity balloon catheter for a medical treatment according to claim 1, further comprising:
a marker positioned in association with the non-branching distal end portion of the single intra-cavity catheter configured to at least one of locate or position the single intra-cavity catheter within the body cavity for the medical treatment.

4. The multi-purpose intra-cavity balloon catheter for a medical treatment according to claim 1, wherein:
at least one other of the plurality of lumens is configured to remove a fluid or a material from an area adjacent to the body cavity.

5. The multi-purpose intra-cavity balloon catheter for a medical treatment according to claim 1, wherein:
at least one other of the plurality of lumens is configured to receive a radioactive material for the medical treatment.

6. The multi-purpose intra-cavity balloon catheter for a medical treatment according to claim 5, wherein:
the radioactive material includes at least one of a radioactive wire or a radioactive seed.

7. The multi-purpose intra-cavity balloon catheter for a medical treatment according to claim 5, wherein:
the radioactive material is selected from the group consisting of Ir-192, Au-198, I-125 and Cs-131.

8. The multi-purpose intra-cavity balloon catheter for a medical treatment according to claim 5, wherein:
the radioactive material delivers a dose of radiation ranging from 1 Curie to 10 Curies.

9. The multi-purpose intra-cavity balloon catheter for a medical treatment according to claim 1, wherein:
the body cavity for the medical treatment is selected from the group consisting of an esophagus, a rectum, a vagina and a surgically created cavity.

10. The multi-purpose intra-cavity balloon catheter for a medical treatment according to claim 1, wherein: the single intra-cavity catheter comprises polyurethane.

11. The multi-purpose intra-cavity balloon catheter for a medical treatment according to claim 1, wherein: the at least one inflatable balloon in each of the plurality of balloon groups has a shape selected from the group consisting of a cylindrical shape, a rectangular shape, an oval shape and a spherical shape.

12. The multi-purpose intra-cavity balloon catheter for a medical treatment according to claim 1, wherein: the at least one inflatable balloon in each of the plurality of balloon groups is made of a material selected from the group consisting of nylon, polyurethane, polyether block amide, polyethylene terephthalate or combinations thereof.

13. The multi-purpose intra-cavity balloon catheter for a medical treatment according to claim 1, wherein: at least one portion of the single intra-cavity catheter or the at least one inflatable balloon in at least one balloon group of the plurality of balloon groups is coated with a medicinal agent for releasing the medicinal agent internally to a predetermined location in the body cavity in association with or for the medical treatment.

\* \* \* \* \*